US011183274B2

(12) United States Patent
Horiuchi et al.

(10) Patent No.: US 11,183,274 B2
(45) Date of Patent: Nov. 23, 2021

(54) ANALYSIS OF ANSWERS TO QUESTIONS

(71) Applicant: INTERNATIONAL BUSINESS MACHINES CORPORATION, Armonk, NY (US)

(72) Inventors: Yoshio Horiuchi, Hiratsuka (JP); Katsuhiko Hagiwara, Chuorinkan (JP); Yuji Sugiyama, Tokyo (JP); Chiaki Oishi, Yokohama (JP); Jiayun Zhu, Tokyo (JP); Junichi Sugimoto, Yokohama (JP)

(73) Assignee: International Business Machines Corporation, Armonk, NY (US)

( * ) Notice: Subject to any disclaimer, the term of this patent is extended or adjusted under 35 U.S.C. 154(b) by 623 days.

(21) Appl. No.: 15/844,682

(22) Filed: Dec. 18, 2017

(65) Prior Publication Data

US 2019/0189251 A1 Jun. 20, 2019

(51) Int. Cl.
*G16H 10/20* (2018.01)
*G16H 50/20* (2018.01)
(Continued)

(52) U.S. Cl.
CPC .............. *G16H 10/20* (2018.01); *A61B 5/68* (2013.01); *G06N 20/00* (2019.01); *G16H 10/60* (2018.01); *G16H 40/63* (2018.01); *G16H 50/20* (2018.01)

(58) Field of Classification Search
CPC ........ G16H 10/20; G16H 10/60; G16H 50/20; G16H 40/63; G06N 20/00; A61B 5/68
See application file for complete search history.

(56) References Cited

U.S. PATENT DOCUMENTS

2007/0299696 A1  12/2007  Matsubara et al.
2014/0073882 A1*  3/2014  Choi ...................... G16H 50/20
                                                      600/301
(Continued)

FOREIGN PATENT DOCUMENTS

JP    2003196394 A    7/2003
JP    2003323488 A    11/2003
(Continued)

OTHER PUBLICATIONS

Harlin et al., "Using a Structured, Computer-Administered Questionnaire for Evaluating Health-Related QOL with Chronic Lower Extremity Wounds", Ostomy Wound Management, Issue No. vol. 55, Issue 9, Sep. 2009, pp. 1-19.
(Continued)

*Primary Examiner* — Fonya M Long
*Assistant Examiner* — Anthony Michael Balaj
(74) *Attorney, Agent, or Firm* — Robert R. Aragona

(57) ABSTRACT

The present invention provides a method for analyzing answers to questions in an electronic document. The method comprises reading, into a memory, the user's answers to the questions and a user's answer history information from the user's answers, wherein the user's answer history information is collected at the time the questions are answered. The method further comprises inputting, into a machine learning model, the user's answers to the questions and the user's answer history information from the user's answers to output an analysis result, wherein the machine learning model is trained, in advance, using one or more sets of training data, each set of training data comprising one or more answers to one or more questions and answer history information from the one or more answers, and a correct result which is obtained by manually judging the one or more answers to the one or more questions.

18 Claims, 20 Drawing Sheets

(51) Int. Cl.
*A61B 5/00* (2006.01)
*G16H 10/60* (2018.01)
*G06N 20/00* (2019.01)
*G16H 40/63* (2018.01)

(56) References Cited

U.S. PATENT DOCUMENTS

| | | | |
|---|---|---|---|
| 2014/0122109 A1* | 5/2014 | Ghanbari | G16H 10/20 |
| | | | 705/2 |
| 2014/0229199 A1 | 8/2014 | Beckley | |
| 2015/0120319 A1 | 4/2015 | Wilson et al. | |
| 2016/0335399 A1 | 11/2016 | Vancho | |
| 2017/0039523 A1* | 2/2017 | Rotimi | H04L 63/0861 |
| 2018/0114455 A1* | 4/2018 | Brecknell | G06F 21/552 |
| 2018/0315488 A1* | 11/2018 | Miranda | G16H 50/30 |

FOREIGN PATENT DOCUMENTS

| | | |
|---|---|---|
| JP | 2011067501 A | 4/2011 |
| JP | 2014089650 A | 5/2014 |
| WO | 2014186780 A1 | 11/2014 |

OTHER PUBLICATIONS

Pincus, "Electronic Multidimensional Health Assessment Questionnaire (eMDHAQ): past, present and future of a proposed single data management system for clinical care, research, quality improvement, and monitoring of long-term outcomes", 2016, vol. 34, No. 5, Suppl. 101—P1 0017, PF 0033, pp. 1-19.

* cited by examiner

Interview Sheet

Q1. Do you have something to worry about ?

☐ All times  ☐ Sometimes  ☐ No

Q2. What area of your head hurts ?

☐ Front  ☐ Back  ☐ Right Side  ☐ Left Side  ☐ Entire head

Q3. Type of pain ?

☐ Throbbing  ☐ Sharp/severe  ☐ Like being struck with a hammer

☐ Tringling  ☐ Pricking  ☐ Others

Q4. Does your physical condition change when you take a medicine ?.

ANALYSIS OF ANSWERS TO QUESTIONS

BACKGROUND

The present invention relates to an analysis of answers to questions, and more specifically, to a technique for analyzing answers to questions in an electronic document, using a machine learning model.

Digitalization of medical records is becoming common in the medical field. As such, medical interview systems using electronic devices, such as tablets, pads, smart phones, and kiosk terminals, are expected to become more prevalent.

SUMMARY

According to one aspect of an embodiment of the present invention, the embodiment of the present invention provides a computer-implemented method for analyzing answers to questions in an electronic document.

In one embodiment, the method comprises reading, into a memory, user's answers to the questions and answer history information on the user's answers; and inputting, into a machine learning model, the user's answers and the answer history information on the user's answers to output an analysis result. The answer history information was collected at the time when the questions were answered. The machine learning model was in advance trained using plural sets of training data. Each training data comprises answers to the questions and answer history information on the answers, an analysis result which was output by inputting the answers to the questions and the answer history information into the machine learning model in training, and, if exists, a result which was obtained by manually judging the answers to the questions. This manually obtained result is regarded as a correct data of analyzing the answers to the questions.

In another embodiment, the method comprises reading, into a memory, user's answers to the questions and answer history information on the user's answers; inputting the user's answers into a first machine learning model to output a first analysis result; and inputting, into a second machine learning model, the user's answers, the answer history information on the user's answers, and the first analysis result itself or manually judged result of the user's answers to the questions to output a second analysis result. The answer history information was collected at the time when the questions were answered. The first machine learning model was in advance trained using plural sets of training data. Each training data for the first machine learning model comprises answers to the questions, an analysis result which was output by inputting the answers to the questions into the first machine learning model in training, and a result which was obtained by manually judging the answers to the questions. This manually obtained result is regarded as a correct data of the first machine learning model and of analyzing the answers to the questions. The second machine learning model was in advance trained using plural sets of training data. Each training data comprises answers to the questions, answer history information on the answers, an analysis result which was output by inputting, into the first machine learning model, the answers to the questions and answer history information on the answers, an analysis result which was an output of the second machine learning model in training, and, if exists, a result which was obtained by manually judging the answers to the questions. This manually obtained result is regarded as a correct data of the second machine learning model and of analyzing the answers to the questions.

In another embodiment, the method comprises reading, into a memory, user's answers to the questions and answer history information from the user's answers; inputting, into a first machine learning model, the user's answers and the answer history information on the user's answers to output a first analysis result; and inputting, into a second machine learning model, the user's answers, the answer history information on the user's answers, and the first analysis result itself or manually judged result of the user's answers to the questions to output a second analysis result. The answer history information was collected at the time when the questions were answered. The first machine learning model was in advance trained using plural sets of training data. Each training data for the first machine learning model comprises answers to the questions and answer history information on the answers, an analysis result which was output by inputting, into the first machine learning model in training, the answers to the questions and answer history information on the answers, and a result which was obtained by manually judging the answers to the questions. This manually obtained result is regarded as a correct data of the first machine learning model and of analyzing the answers to the questions. The second machine learning model was in advance trained using plural sets of training data. Each training data for the second machine learning model comprises answers to the questions, answer history information on the answers, an analysis result which was output by inputting, into the first machine learning model, the answers to the questions and answer history information on the answers, an analysis result which was an output of the second machine learning model in training, and, if exists, a result which was obtained by manually judging the answers to the questions. This manually obtained result is regarded as a correct data of the second machine learning model and of analyzing the answers to the questions.

According to another aspect of an embodiment of the present invention, a system, such as a computer system, comprising a computer readable storage medium storing a program of instructions executable by the computer system to perform one or more methods described herein also may be provided.

According to another aspect of an embodiment of the present invention, a computer program product comprising a computer readable storage medium storing a program of instructions executable by the computer system to perform one or more methods described herein also may be provided.

BRIEF DESCRIPTION OF THE DRAWINGS

The disclosure will provide details in the following description of preferred embodiments with reference to the following figures.

FIG. 2A depicts an electronic document, such as a medical interview questionnaire, in accordance with an embodiment of the present invention.

DETAILED DESCRIPTION

Figure 1:
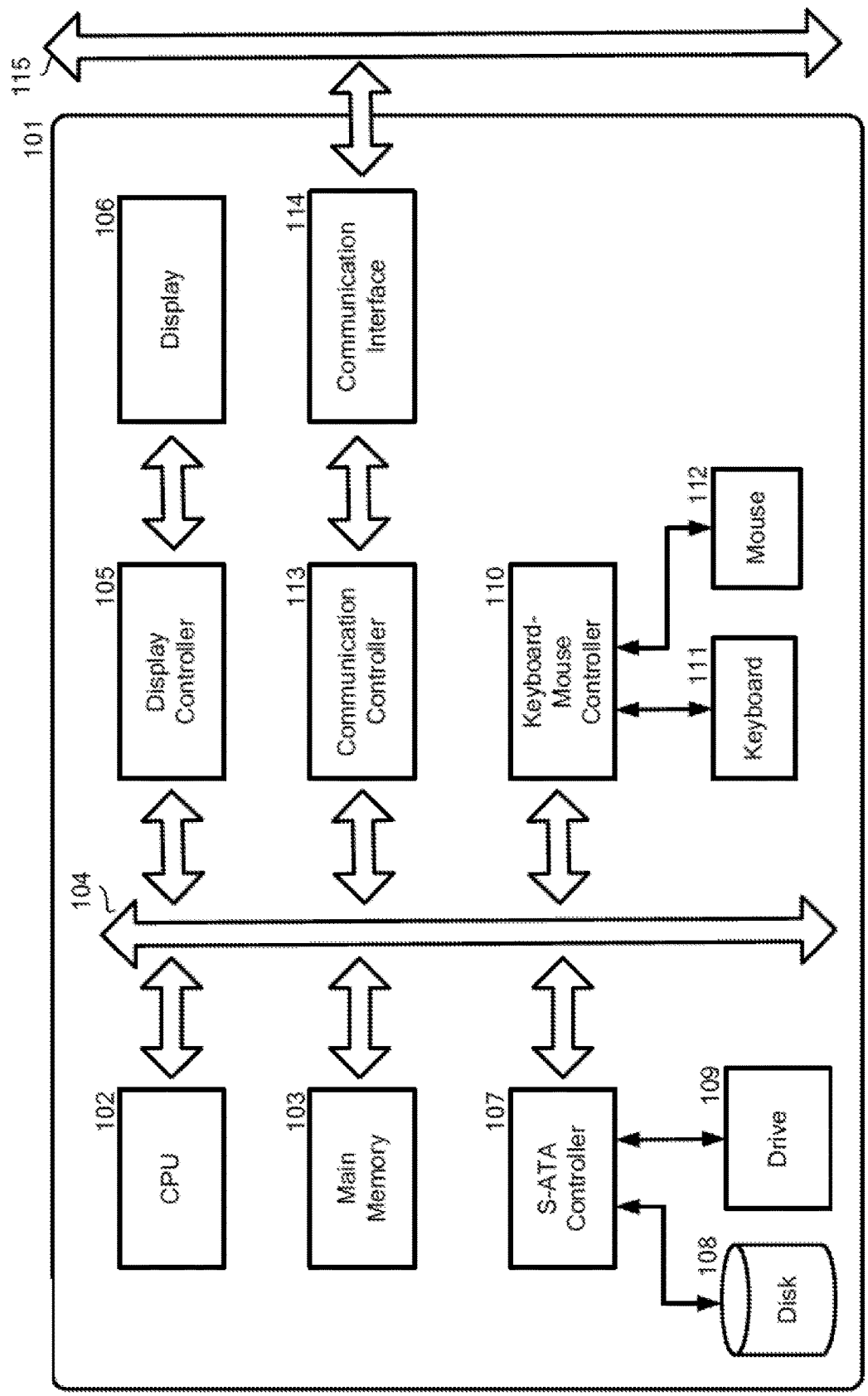
FIG. 1 depicts a basic block diagram of computer hardware used in accordance with an embodiment of the present invention.

The descriptions of the various embodiments of the present invention have been presented for purposes of illustration, and are not intended to be exhaustive or limited to the embodiments disclosed herein. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

To define more clearly the terms used herein, the exemplified definitions are provided hereinafter, but the meaning of the terms should be interpreted broadly as known to the technical field to which the present invention relates.

An "electronic document", may refer to any document having one or more questions implemented as electrical data. The one or more questions may be, for example, but not limited to, a closed question, a multiple-choice question, a self-completed questionnaire, or a combination thereof. One or more questions in the electronic document may be presented on a display device or a display embedded in an electronic device, such as a tablet computer, a pad, a smart phone, or a kiosk terminal.

A "machine learning model", may generate predictions for multiple classes (or predict one of more than two outcomes) when a machine learning algorithm is trained with a training data-set. The machine learning model may be, for example, a neural network, such as Convolutional Neural Networks (CNN), Recurrent Neural Networks (RNN) or their varieties.

A neural network may generally have an input layer, hidden layers and an output layer. The input layer is not composed of full neurons, but rather consists simply of the values in a data record, which constitutes inputs to the next layer of neurons. The next layer is called a hidden layer; there may be several hidden layers. The final layer is the output layer, where there is one node for each class. A single sweep forward through the network results in the assignment of a value to each output node, and the record is assigned to the class's node that has the highest value.

The neural network processes records one at a time, and learns by comparing the initial classification of the record (which, at the outset, is largely arbitrary) with the actual known classification of the record. The errors from the initial classification of a first record is fed back into the network and used to modify the network's algorithm the second time around, and so on for many iterations.

In the training phase of the neural network, one or more sets of training data are used to adjust parameters, such as weights and/or bias in the hidden layers. A set of training data is used, as supervised training data, for a correct class for each record. A correct class for each record is known (i.e. manually judged), and the output nodes can therefore be assigned correct values—"1" for the node corresponding to the correct class, and "0" for the others. It is thus possible to compare the neural network's calculated values for the output nodes to these correct values, and calculate an error term for each node. These error terms are then used to adjust the weights in the hidden layers so that the next time around the output values will be closer to the correct values.

A key feature of the neural network is an iterative learning process in which data cases (rows) are presented to the neural network one at a time, and the weights and/or bias associated with input values are adjusted each time. After all cases are presented, the process often starts over again. During this training phase, the neural network learns by adjusting the weights so as to be able to predict the correct class label of input samples. The neural network learning is also referred to as connectionist learning, due to connections between the units. Advantages of the neural network include their high tolerance to noisy data, as well as their ability to classify patterns on which they have not been trained.

Many algorithms for training the neural network are known in the art and can be used for training an embodiment of the present invention. The most popular neural network algorithm is known as a back-propagation algorithm, proposed in the 1980's. The back-propagation algorithm is a method used in the neural network to calculate error contribution of each neuron after a batch of data is received. The back propagation requires a known, desired output for each input value, such as training data having a correct answer. Therefore, the back-propagation is considered to be a supervised learning method.

FIG. 1 illustrates a basic block diagram of computer hardware used in accordance with an embodiment of the present invention.

A computer (101) may be, for example, but is not limited to, a desktop, a laptop, a notebook or a server computer. The server computer may be, for example, but is not limited to, a workstation, a rack-mount type server, a blade type server, a mainframe server, or a cloud server and may run, for example, a hypervisor for creating and running one or more virtual machines. The computer (101) may comprise one or more CPUs (102) and a main memory (103) connected to a bus (104). The CPU (102) may be preferably based on a 32-bit or 64-bit architecture. The CPU (102) may be, for example, but is not limited to, the Power® series of International Business Machines Corporation; the Core i™ series, the Core 2™ series, the Atom™ series, the Xeon™ series, the Pentium® series, or the Celeron® series of Intel Corporation; or the Phenom™ series, the Athlon™ series, the Turion™ series, or Sempron™ of Advanced Micro Devices, Inc. ("Power" is registered trademark of International Business Machines Corporation in the United States, other countries, or both; "Core i", "Core 2", "Atom", and "Xeon" are trademarks, and "Pentium" and "Celeron" are registered trademarks of Intel Corporation in the United States, other countries, or both; "Phenom", "Athlon", "Turion", and "Sempron" are trademarks of Advanced Micro Devices, Inc. in the United States, other countries, or both).

A display (106) such as a liquid crystal display (LCD) may be connected to the bus (104) via a display controller (105). The display (106) may be used to display, for management of the computer(s), information on a computer connected to a network via a communication line and information on software running on the computer using an appropriate graphics interface. The display may have a touch screen or a non-touch screen. The display may be for example, but not limited to, a LCD, PDP, OEL or a projection type display. A disk (108) such as a hard disk or a solid state drive, SSD, and a drive (109) such as a CD, a DVD, or a BD (Blu-ray disk) drive may be connected to the bus (104) via an SATA or IDE controller (107). Moreover, a keyboard (111) and a mouse (112) may be connected to the bus (104) via a keyboard-mouse controller (110) or USB bus (not shown).

An operating system, programs providing Windows®, UNIX® Mac OS®, Linux®, or a Java® processing environment, Java® applications, a Java® virtual machine (VM), and a Java® just-in-time (JIT) compiler, such as J2EE®, other programs, and any data may be stored in the disk (108) to be loadable to the main memory. ("Windows" is a registered trademark of Microsoft corporation in the United States, other countries, or both; "UNIX" is a registered trademark of the Open Group in the United States, other countries, or both; "Mac OS" is a registered trademark of Apple Inc. in the United States, other countries, or both; "Linux" is a registered trademark of Linus Torvalds in the United States, other countries, or both; and "Java" and "J2EE" are registered trademarks of Oracle America, Inc. in the United States, other countries, or both).

The drive (109) may be used to install a program, such as the computer program of an embodiment of the present invention, readable from a CD-ROM, a DVD-ROM, or a BD to the disk (108) or to load any data readable from a CD-ROM, a DVD-ROM, or a BD into the main memory (103) or the disk (108), if necessary.

A communication interface (114) may be based on, for example, but is not limited to, the Ethernet® protocol. The communication interface (114) may be connected to the bus (104) via a communication controller (113), physically connects the computer (101) to a communication line (115), and may provide a network interface layer to the TCP/IP communication protocol of a communication function of the operating system of the computer (101). In this case, the communication line (115) may be a wired LAN environment or a wireless LAN environment based on wireless LAN connectivity standards, for example, but is not limited to, IEEE® 802.11a/b/g/n ("IEEE" is a registered trademark of Institute of Electrical and Electronics Engineers, Inc. in the United States, other countries, or both).

Hereinafter, the various embodiments of the present invention will be described with reference to FIGS. 2A and 2B, FIGS. 3A and 3B, FIGS. 4A to 4C, FIGS. 5A to 5C, FIGS. 6A and 6B, FIGS. 7A and 7B, FIGS. 8A and 8B, and FIGS. 9A to 9C.

An embodiment of the present invention is based on the following perceptions. When a user inputs or reviews an answer, some hesitation by the user to answer the question may be observed or a certain question may be set aside, by the user, to answer or review. These actions are not considered when a doctor consults a user as a patient, face to face. However, these actions may have some meaning when analyzing an answer to the question. Accordingly, it is desirable to record such actions when analyzing a user's answers to questions.

Figure 2B:
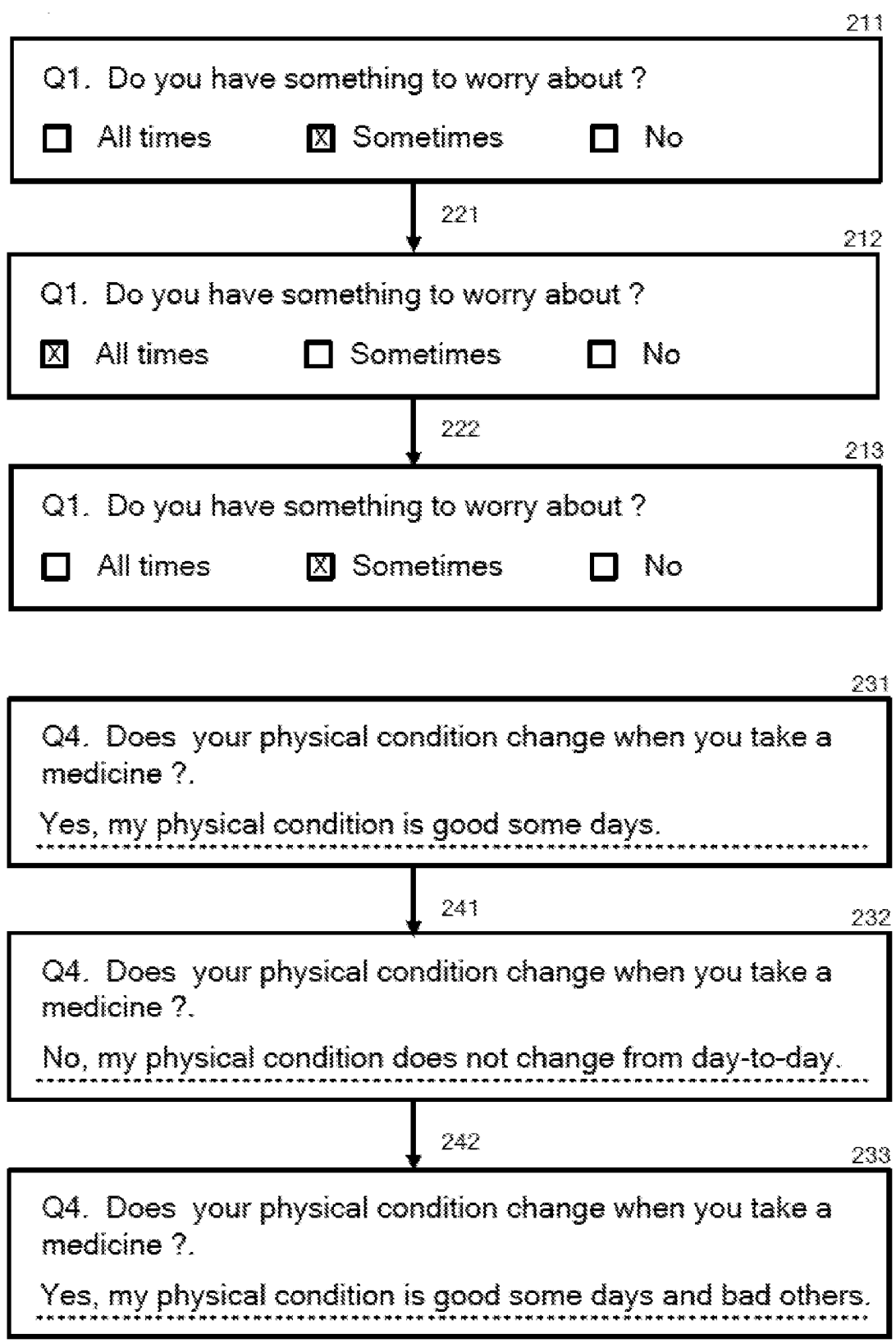
FIG. 2B depicts a completed medical interview questionnaire, in accordance with an embodiment of the present invention.

FIGS. 2A and 2B depict an electronic document, in accordance with an embodiment of the present invention.

FIG. 2A depicts an electronic document, such as a medical interview questionnaire, in accordance with an embodiment of the present invention. The electronic document (201) is a kind, or type, of a medical interview sheet, or questionnaire. The electronic document (201) may be displayed on a display associated with a device of a user (hereinafter also referred to as "user device") who answers a question.

The electronic document (201) has a plurality of questions, such as closed questions: Q1, multiple-choice questions: Q2 and Q3, and a self-completed questionnaire, Q4.

For Q1, a user may select one answer among three choices, for example, using a mouse or by touching a square icon associated with the answer.

For Q2 and Q3, the user may select one or more answers among multiple choices, for example, using a mouse or by touching a square icon associated with the answer.

For Q4, the user may input answer to the Q4, for example, using a keyboard, a virtual keyboard or by inputting an answer through a microphone.

FIG. 2B depicts a completed medical interview questionnaire, in accordance with an embodiment of the present invention.

At the time when the user inputs or reviews an answer, the user may input or review the answer displayed on the display associated with the user device and optionally modify or change the answer.

The embodiments (211 to 213) show that the user first selected the answer, "sometimes" (211), and then reselected (221) the answer, "All times" (212), and finally reselected (222) the answer, "sometimes" (213).

The embodiments (231 to 233) show that the user first input "Yes, my physical condition is good some days." (231), then modified (241) the answer, "No, my physical condition does not change from day-to-day." (232), and finally modified (242) "Yes, my physical condition is good some days and bad others." (233).

During inputting or reviewing of the answers, the user device may collect information on answering which is generated by an answer operation by the user. The information on answering may be stored in a storage associated with the user device or a storage from which a system according to an embodiment of the present invention can obtain the information on answering.

The information on answering may be used itself as answer history information from answers, such as answer history information from a user's answers, or may be processed to generate answer history information. In the latter case, the generation of the aforesaid answer history information is generated based on the information of the answer. The generation may be done on the user device or the system, according to an embodiment of the present invention.

The answer history information may include, for example, but not limited to, (i) information on an answering order of questions, (ii) information on the time required for answering the question, (iii) information on the number of times or frequency that the answer to the question was changed, or a combination thereof.

It is known that an answering order of questions, the time required for answering a question, or the number of times (i.e. frequency) that the user answers the question may affect the likelihood of answers (see US2003092976 A1, JP2011067501 A, and JP2012005632 A, if necessary). Accordingly, there exists a relationship between answer history information on answers, within a questionnaire, and a result which is obtained by manually judging the answers to the questions, such as a diagnosis result. Subject matter experts, such as medical professionals, may manually judge the answers to questions, in a training data set, in order to provide accurate results.

The answer history information may be obtained at the time when each of the answers in an electronic document is input or reviewed by a person such as a user.

An embodiment of the answer history information will be explained in detail below, by referring to FIGS. 2A and 2B.

(i) Information on an answering order of questions may be, for example, the order made by the user when the answers were input or reviewed; or the order faster or slower than the predetermined reference order, N, where N is a positive integer. Let us suppose that questions in an electronic document are, for example, Q1 to Q4 described in FIG. 2A. Further, let us suppose that, in this case, the normal answering order to answer the questions is set to as follows: Q1, Q2, Q3 and then Q4. Further, let us suppose that the user answers the questions in the order of Q2, Q3, Q1 and then finally Q4. In the former embodiment of the order made by the user when the answers were input or reviewed, the answering order of questions, Q1 to Q4, may be recorded as follows: Q2, Q3, Q1 and then finally Q4. In the latter embodiment of the order faster or slower than the predetermined reference order, the answering order of questions, Q1 to Q4, may be recorded as follows: Q1 (+2 order), Q2 (−1 order), Q3 (−1 order) and Q4 (+0 order).

For example, in a case where the electronic document is a medical interview questionnaire or a medical examination questionnaire, a user may tend to not answer questions in sequence. Accordingly, information on an answering order of questions may be useful for analyzing answers to questions, for example, for improving accuracy of a medical diagnosis result.

(ii) Information on the time required for answering the question may be, for example, the time required for inputting or reviewing each of the answers; or the time required for inputting or reviewing an answer longer or shorter than the predetermined reference answering time, where T is a positive integer. Let us suppose that questions in an electronic document are, for example, Q1 to Q4 described in FIG. 2A. Further, let us suppose that, in this case, the standard time of answering the questions, Q1 to Q4, may be set to as follows: Q1=25 s, Q2=60 s, Q3=65 s and Q4=130 s. In the former embodiment of the time required for inputting or reviewing each of the answers, information on the time required for answering the question is as follows: Q1=30 s, Q2=50 s, Q3=75 s, and Q4=150 s. A latter embodiment of information on the time required for answering the question is as follows: Q1 (+5 s), Q2 (−10 s), Q3 (+10 s) and Q4 (+20 s), if the real time of answering the questions is as follows: Q1=30 s, Q2=50 s, Q3=75 s, and Q4=150 s.

For example, in a case where the electronic document is a medical interview questionnaire or a medical examination questionnaire, a user may tend to need more time to answer each question, depending on a type of question. Accordingly, information on the time required for answering the question may be useful for analyzing answers to questions, for example, for improving accuracy of a medical diagnosis result.

(iii) Information on the number of times or frequency that the answer to the question was changed may be, for example, the number of times or frequency based on the information obtained at the time when the user inputs or reviews the answer; or the number of times or frequency larger or smaller than the predetermined reference answering number of times or frequency. Let us suppose that questions in an electronic document are, for example, Q1 to Q4 described in FIG. 2A. Further, let us suppose that, in this case, the standard numbers of times may be set to as follows: Q1=1 time, Q2=2 times, Q3=3 times and Q4=1 time. In the former embodiment of the number of times or frequency based on the information obtained at the time when the user inputs, the information on the number of times or frequency is as follows: Q1=2 times, Q2=1 times, Q3=3 times, and Q4=2 times. In the latter embodiment of the number of times or frequency larger or smaller than the predetermined reference answering number of times or frequency, the information on the number of times or frequency is as follows: Q1=+1 times, Q2=−1 time, Q3=+0 time, and Q4=+1 time, if the real number of times is as follows: Q1=2 times, Q2=1 times, Q3=3 times, and Q4=2 times.

The information on the number of times or frequency can be obtained, for example, by the following methods (A) and (B).

The method (A): In a case where a question is a self-completed questionnaire, one of the following events (a) to (c) may be detected and then the text field is treated as being provisionally fixed.

(a) input or touch operation has been suspended for a predetermined period of time;

(b) input or touch focus is removed from the text field; or (c) another window or application has been activated.

The method (B): In a case where a question is a self-completed questionnaire, the content of the text field is analyzed every time that the text field is provisionally fixed. The content is analyzed using the existing technique, such as a tone analyzer, a sentimental analysis API, a feature term extraction, or a combination thereof.

As exemplified in FIG. 2B, embodiments (231 and 232), the user's answer changes when providing an answer to the same exact question (i.e. from the embodiment (231) to the embodiment (232)). The change (241) of the contents within the user's answer may be analyzed by the existing technique and the following analysis result may be obtained: the answer was changed from a positive answer to a negative answer. Accordingly, it is concluded that the number of times that the answer to the question was changed is +1.

Similarly, in the embodiments (232 and 233), the user's answer changes (242) from the embodiment (232) to the embodiment (233), in response to the same exact question. The change (241) of the contents within the user's answer may be analyzed by the existing technique and the following analysis result may be obtained: the answer was changed from a negative answer to a positive answer. Accordingly, it is concluded that the number of times that the answer to the question was changed is +1.

Accordingly, in the embodiments (231 to 233) in FIG. 2B, the information on the number of times or frequency that the user's answer to the same question was changed is two.

For example, in a case where the electronic document is a medical interview questionnaire or a medical examination questionnaire, a user may tend to change an answer, depending on a type of a question. Accordingly, information on the number of times or frequency that the answer to the question was changed may be useful for analyzing a user's answers to questions, for example, for improving accuracy of a diagnosis result (e.g. a medical diagnosis result).

The answer history information from the user's answers may be generated by normalizing the information on answering, such as anyone of (i) to (iii), into values, 0 to 1, based on a predetermined value.

An embodiment of the normalization may be as follows. Let us suppose the information on the time required for answering the question. The normalized information on the time required for answering the question can be calculated using the following algorithm.

$$\text{If } (t < t_{min}) \{ \\ \quad t_n = 0 \\ \} \text{ else if } (t > t_{max}) \{ \\ \quad t_n = 1 \\ \} \text{ else } \{ \\ \quad t_n = (t - t_{min}) / (t_{max} - t_{min}) \\ \}$$

In the algorithm $t_n$ denotes the normalized information on the time required for answering the question; $t_{min}$ denotes the minimum reference time; and $t_{max}$ denotes the maximum reference time.

During inputting or reviewing the answers, the following information may be further obtained as the answer history information for the user's answers: biometric information on the user's action, sensor information on the user's action or a combination of these. Any known devices for biometric information and/or sensor information detection can be used in an embodiment of the present invention.

An embodiment of the biometric information on the user's action and the sensor information on the user's action will be explained in detail below, by referring to FIGS. 2A and 2B.

Biometric information on the user's action may be, for example, but not limited to, a pulse rate, perspiration of a hand, body temperature, a hand tremor, stress indicator, the degree of concentration, or a combination thereof. The biometric information on the user's action may be obtained at the time when the user's answers are input or reviewed by the user. In a case where a user answers a special question, such as a question which is undesirable to or uncomfortable for a user or a question on which a user does not want to answer, body conditions of the user may change, such as a pulse rate, perspiration of a hand, body temperature, a hand tremor, stress indicator, the degree of concentration or a combination of these. Accordingly, the biometric information may be useful for analyzing a user's answers to questions, for example, for improving accuracy of a diagnosis result (i.e. a medical diagnosis result). Any known method or technique for measuring biometric information can be used in an embodiment of the present invention.

Sensor information on the user may be, for example, but not limited to, location information, speed information, gravity information, or a combination thereof. The sensor information on the user may be obtained at the time when the user's answers are input or reviewed by the user. For example, in a case where the sensor information is location information, the location information may be, for example, "in a hospital" or "in a house". For example, a patient may have varying body conditions (e.g. pulse rate, perspiration, body temperature, etc.) when the patient is in the hospital versus when the patient is in his/her own house. Accordingly, location information may be useful for analyzing a user's answers to questions, for example, for improving accuracy of a diagnosis result. Any sensors known to one of ordinary skill in the art may be used. The sensor may be, for example, but not limited to, a GPS sensor, an acceleration sensor, a gravity sensor, or a combination thereof. In one embodiment, the sensor may be equipped with a device on which a user may answer a question. In another embodiment, the sensor may be equipped with, for example, a chair, a ceiling or a body of a user.

Figure 3A:
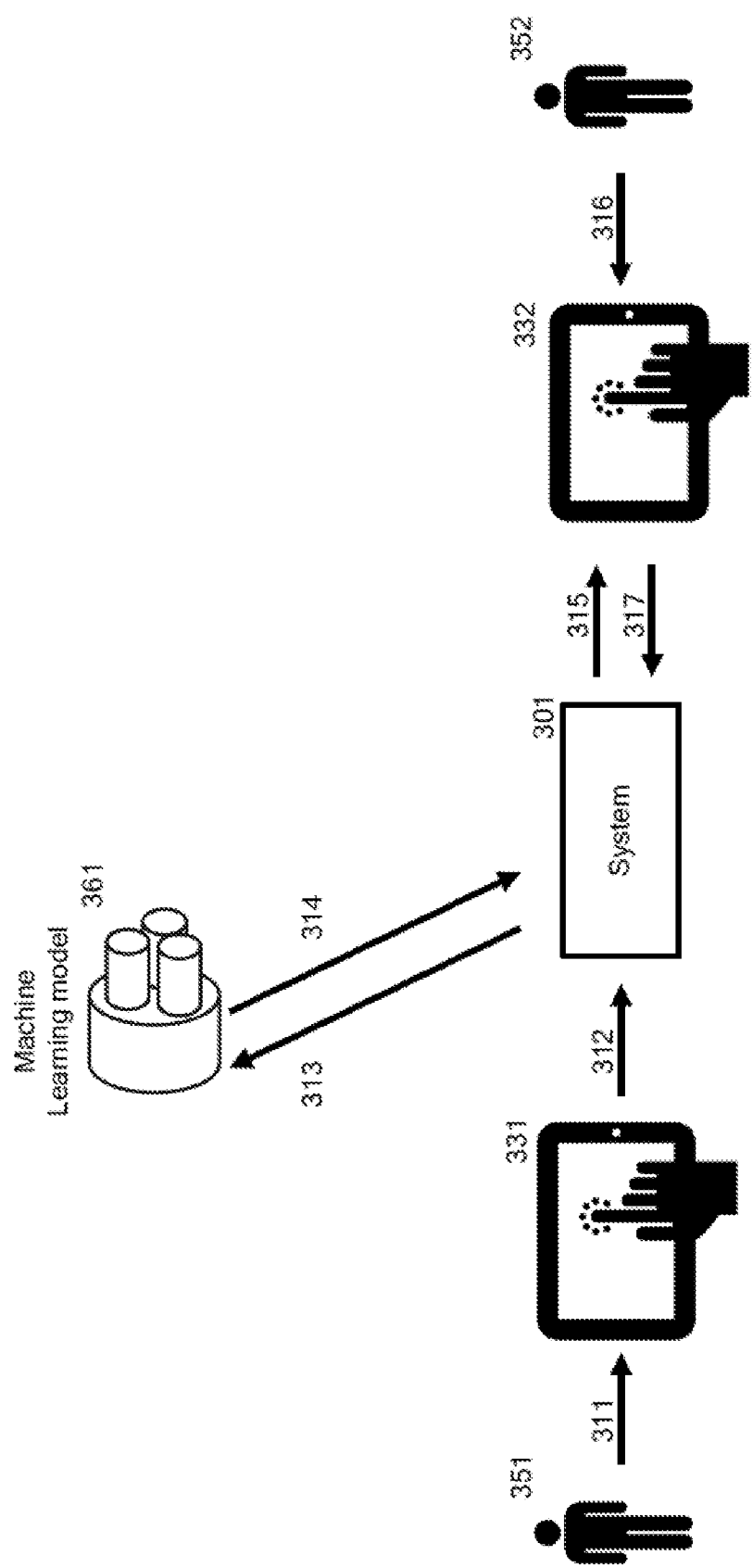
FIG. 3A depicts a flowchart, using a machine learning model, for analyzing answers to questions in an electronic document, in accordance with an embodiment of the present invention.
Figure 4A:
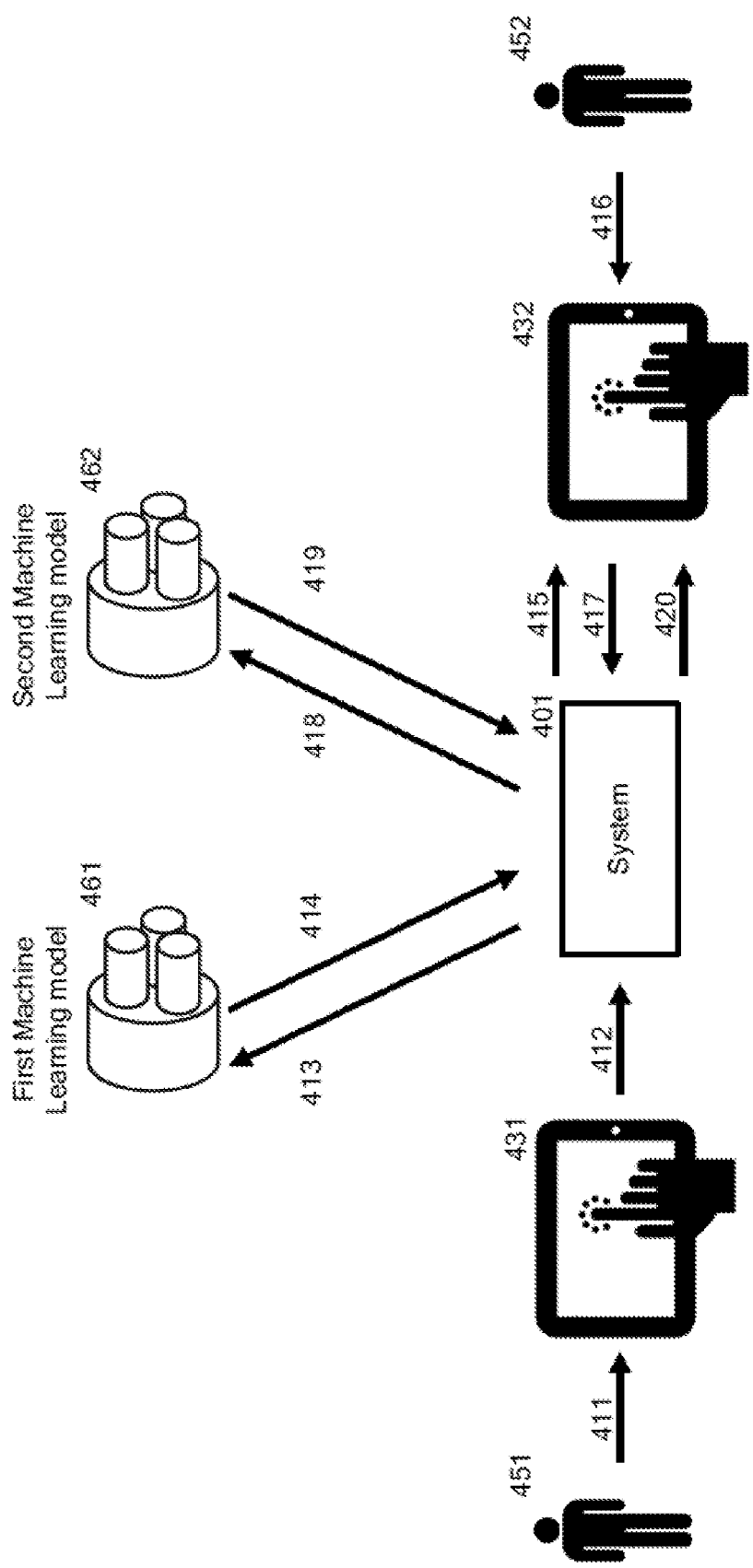
FIG. 4A depicts a flowchart, using a first machine learning model and a second machine learning model, for analyzing answers to questions in an electronic document, in accordance with an embodiment of the present invention.
Figure 5A:
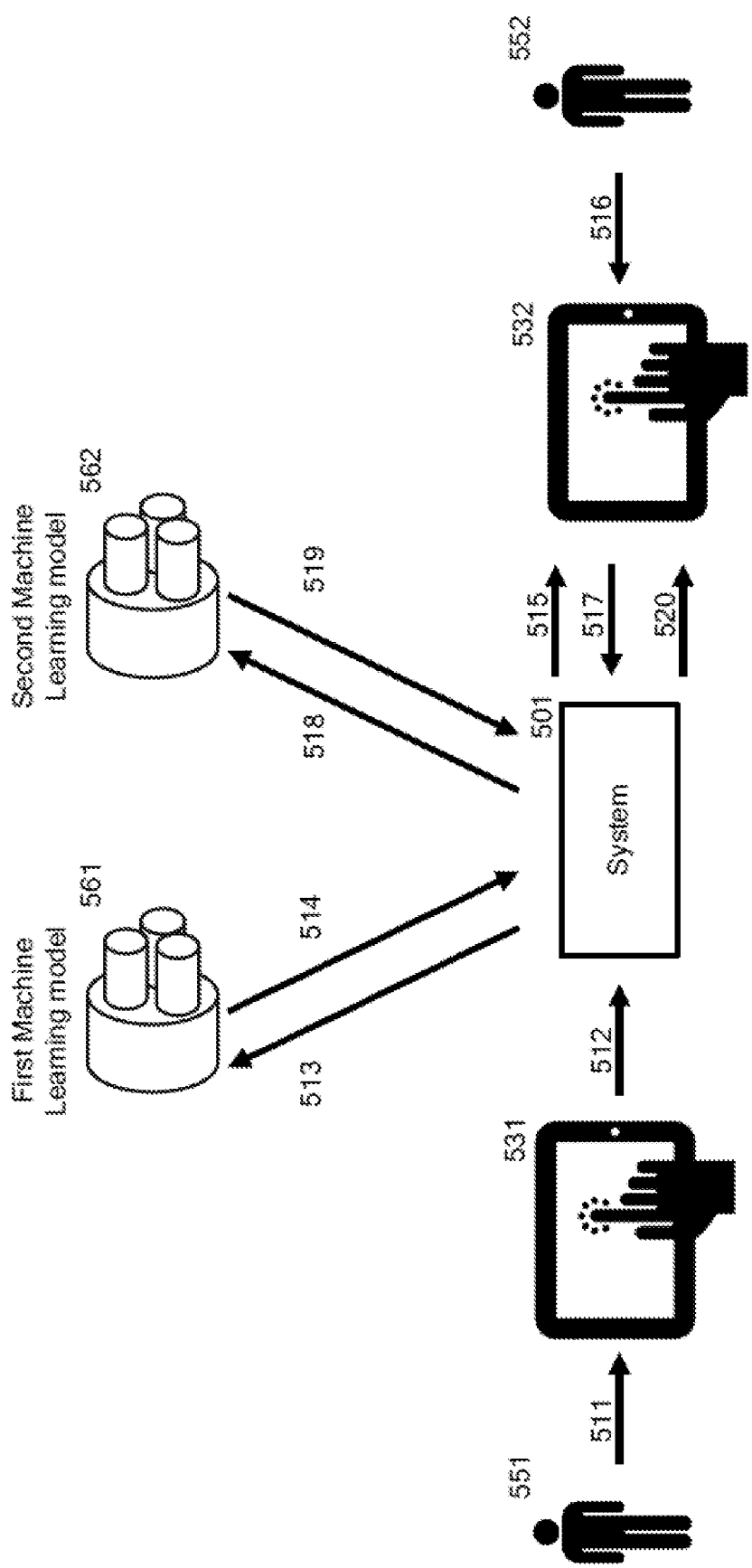
FIG. 5A depicts another flowchart, using a first machine learning model and a second machine learning model, for analyzing answers to questions in an electronic document, in accordance with an embodiment of the present invention.

FIGS. 3A, 4A and 5A depict a flowchart for analyzing answers to questions in an electronic document, in accordance with various embodiments of the present invention.

Figure 3B:
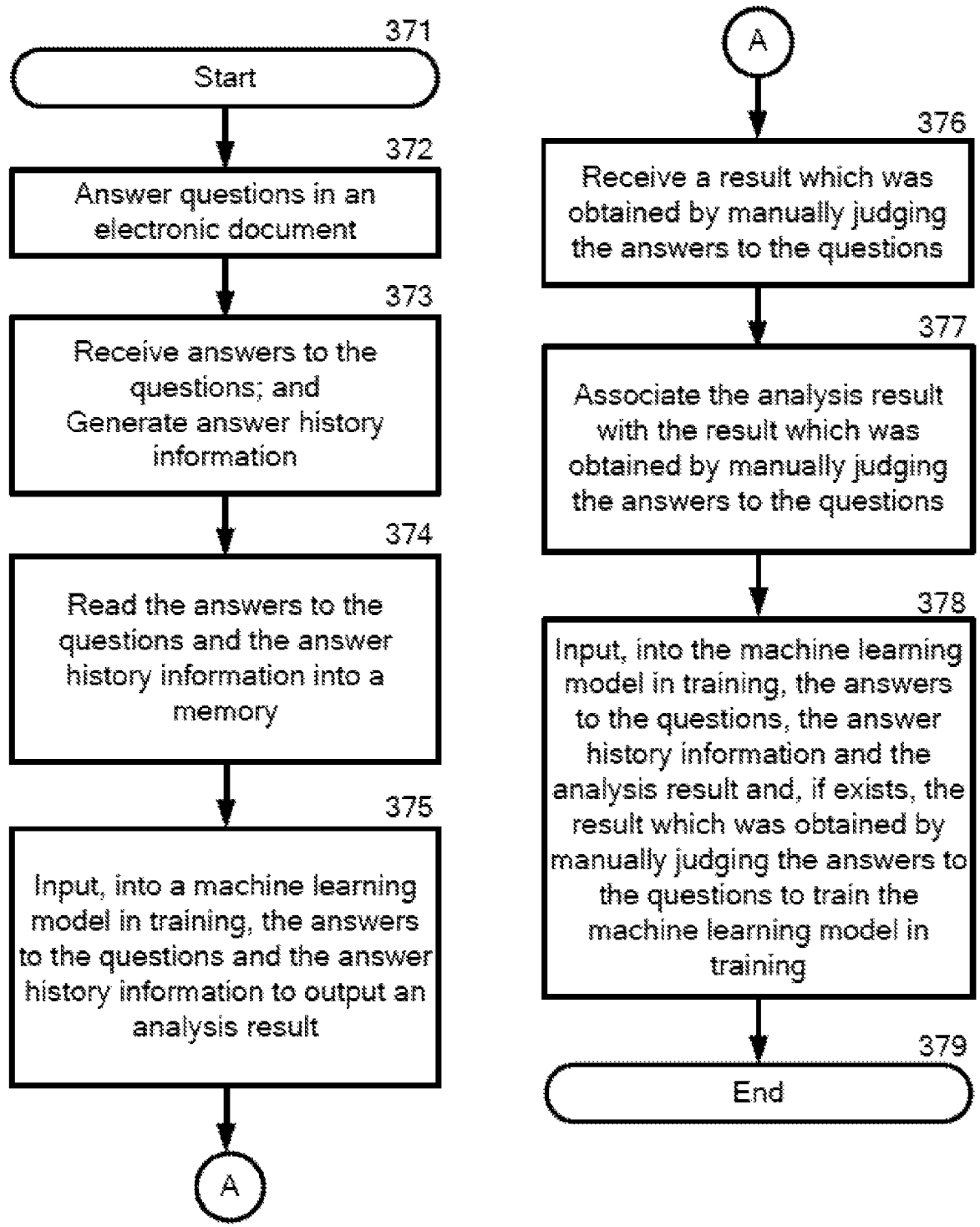
FIG. 3B depicts a flowchart for training a machine learning model, in accordance with an embodiment of the present invention.

FIG. 3B depicts a flowchart for training a machine learning model, as depicted in the embodiment of FIG. 3A.

Figure 4B:
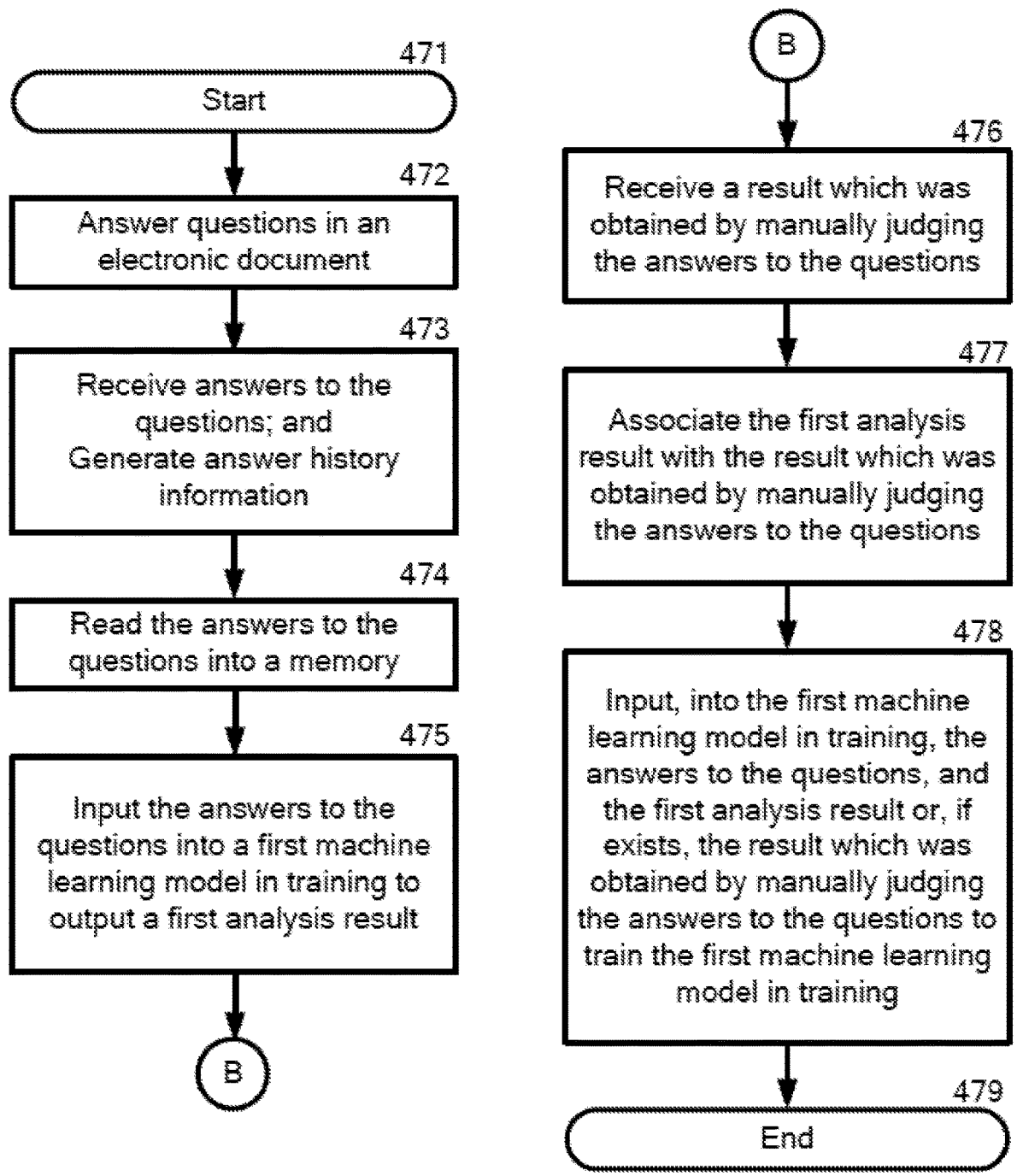
FIG. 4B depicts a flowchart for training a first machine learning model, in accordance with an embodiment of the present invention.

FIG. 4B depicts a flowchart for training a first machine learning model, in accordance with an embodiment of the present invention.

Figure 4C:
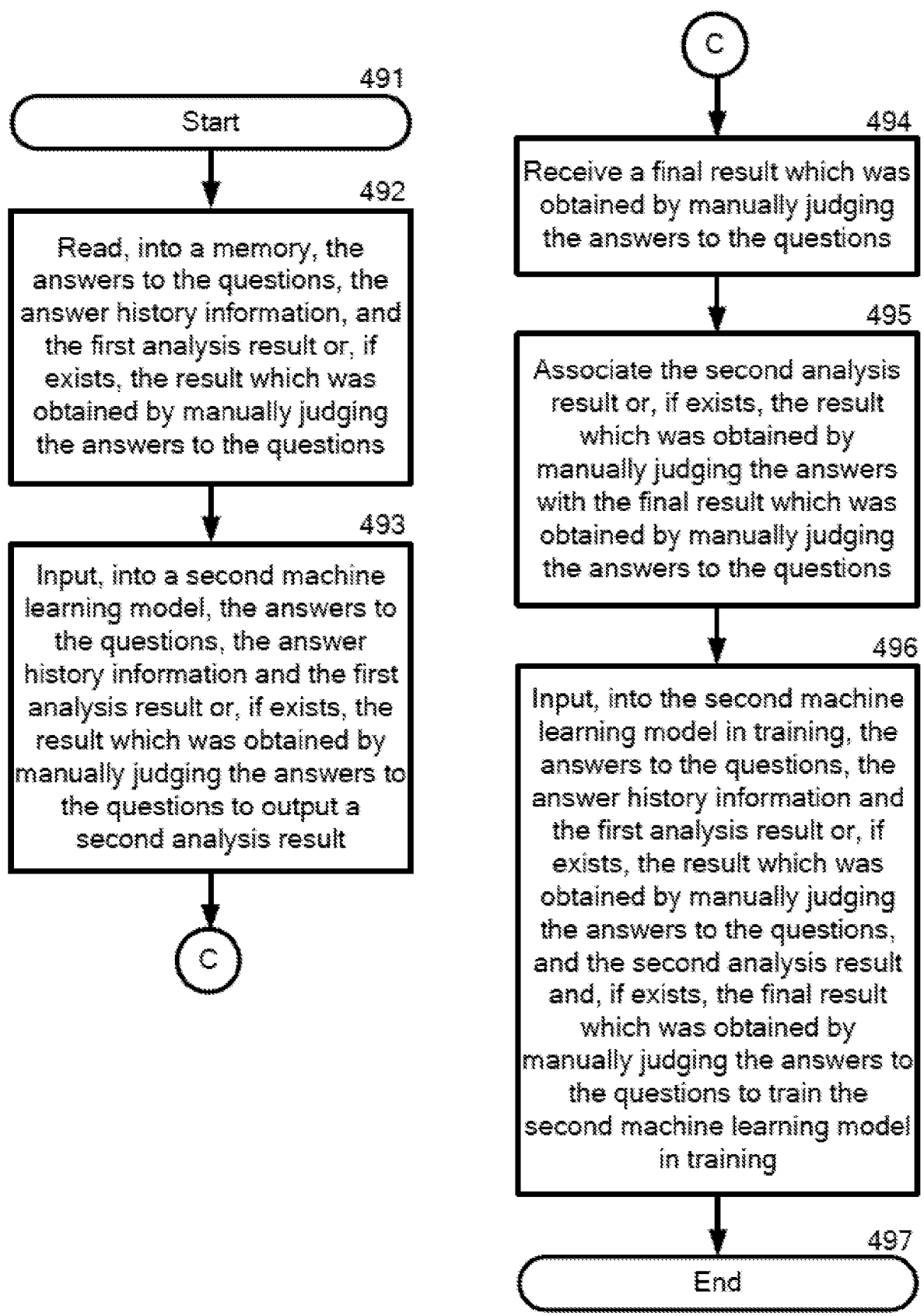
FIG. 4C depicts a flowchart for training a second machine learning model, in accordance with an embodiment of the present invention.

FIG. 4C depicts a flowchart for training a second machine learning model, in accordance with an embodiment of the present invention.

FIGS. 4B and 4C depict flowcharts for training first and second machine learning models, respectively, as depicted in the embodiment of FIG. 4A.

Figure 5B:
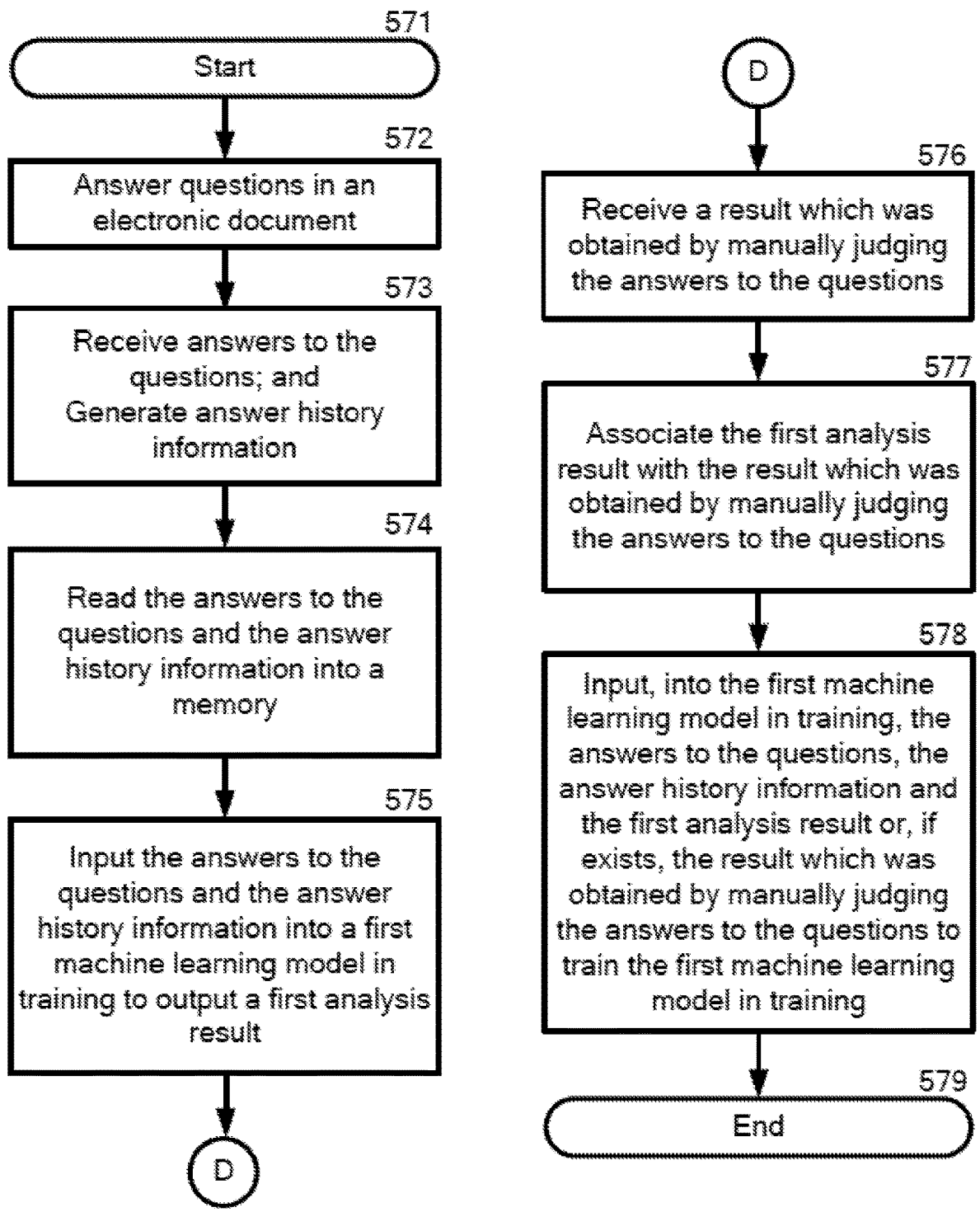
FIG. 5B depicts a flowchart for training a first machine learning model, in accordance with an embodiment of the present invention.

FIG. 5B depicts a flowchart for training a first machine learning model, in accordance with an embodiment of the present invention.

Figure 5C:
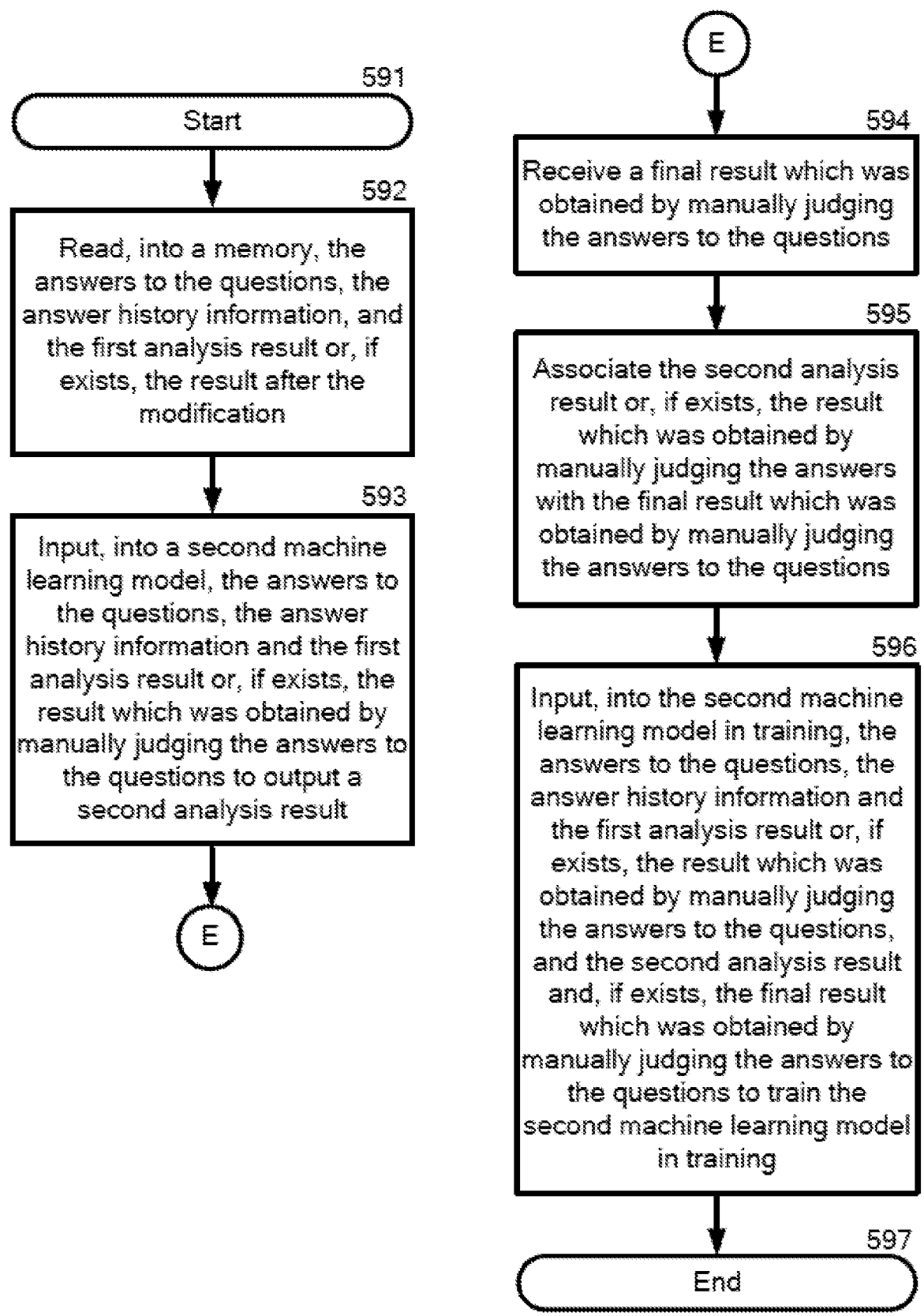
FIG. 5C depicts a flowchart for training a second machine learning model, in accordance with an embodiment of the present invention.

FIG. 5C depicts a flowchart for training a second machine learning model, in accordance with an embodiment of the present invention.

FIGS. 5B and 5C depict flowcharts for training first and second machine learning models, respectively, as depicted in the embodiment of FIG. 5A.

The common matters in the embodiments described in FIGS. 3A, 4A and 5A will be first explained below.

The user device (331, 431 and 531) displays one or more questions in an electronic document on the display associated with the user device (331, 431 and 531). A user (351, 451 and 551) may input or review (311, 411 and 511) answers to questions. Hereinafter, the answer may also be referred to as "a user's answers to the questions". The user device (331, 431 and 531) may be an electronic device, such as a tablet, a pad, a smart phone, or a kiosk terminal.

The user device (331, 431 and 531) receives the user's answers to the questions and collects information on answering which was generated by an answer operation by the user (351, 451 and 551) during inputting or reviewing the answers to the questions.

The user device (331, 431 and 531) may generate answer history information on the user's answers from the information of an answer. Alternatively, the system (301, 401 and 501) may generate answer history information on the user's answers from the information on the answers which were obtained from the user device (331, 431 and 531).

The information on answering is stored in a storage associated with the user device (331, 431 and 531). In one embodiment, the user device (331, 431 and 531) may process the information on answering to generate answer history information for the user's answers and then send (312, 412 and 512) the answer history information for the user's answers to the system (301, 401 and 501), or a storage from which the system (301, 401 and 501) obtains the answer history information for the user's answers. In another embodiment, the user device (331, 431 and 531) sends (312, 412 and 512) the information on answering to the system (301, 401 and 501) and then the system (301, 401 and 501) processes the information on answering to generate answer history information for the user's answers.

A system (301, 401 and 501) corresponds to the computer (101) and may be an embodiment of the present invention. The system (301, 401 and 501) may obtain an analysis result of an answer to the question.

A person (352, 452 and 552) can be presented an analysis result through a device (332, 432 and 532) associated with the person (352, 452 and 552). The person (352, 452 and 552) may modify the analysis result through the device (332, 432 and 532), if necessary.

The device (332, 432 and 532) can present the analysis result. The device (332, 432 and 532) may receive the result which was obtained by manually judging the answers to the questions if the person (352, 452 and 552) modifies the analysis result and sends the result, which was obtained by manually judging the answers to the questions, to the system (301, 401 and 501).

FIG. 3A depicts a flowchart, using a machine learning model, for analyzing answers to questions in an electronic document, in accordance with an embodiment of the present invention.

The machine learning model (361), of FIG. 3A, is in advance prepared and trained according to the embodiment described in FIG. 3B. The embodiment described in FIG. 3B will be first explained below.

The machine learning model (361) may be a model which is trained using one or more sets of training data, for example, by adjusting parameters (e.g. weights and/or bias in hidden layers) in the machine learning model so that the output of the machine learning model is correct data.

Each set of training data may comprise the following (3-i), (3-ii), (3-iii) and (3-iv): (3-i) answers to the questions and (3-ii) answer history information for the answers; and (3-iii) an analysis result which is output by inputting, into the machine learning model in training, (3-i) answers to the questions, (3-ii) answer history information for the answers, and (3-iv) a result which is obtained by manually judging the answers to the questions. This manually obtained result is regarded as correct data, or correct answers, for analyzing the user's answers to the questions. In a case where (3-iv) the manually judged result does not exist, (3-iii) the analysis result may be manually acknowledged, or authorized, as correct data, or correct answers.

The embodiment of the answer history information for the answers may correspond to that of the aforementioned answer history information for the user's answers. Consequently, the answer history information for the answers may include, for example, but not limited to, (i) information on an answering order of questions, (ii) information on the time required for answering the question, (iii) information on the number of times or frequency that the answer to the question was changed, or a combination thereof.

In exemplary embodiments, each set of training data may further comprise the following as the answer history information for the user's answers: biometric information, sensor information, or a combination of these. The aforesaid analysis result may comprise a list of disease names, in a case where the electronic document is a medical interview questionnaire or a medical examination questionnaire. Further, in a case where the medical interview questionnaire or a medical examination questionnaire is associated with a diagnosis and treatment department name, a hospital name, a medicine name, a medical treatment plan, a medical certificate, an inspection name, a medical personnel name, or a combination thereof, the aforesaid analysis result may comprise a diagnosis and treatment department name, a hospital name, a medicine name, a medical treatment plan, a medical certificate, an inspection name, a medical personnel name, or a combination thereof. This analysis result may be obtained in advance from a medical record associated with a medical interview questionnaire or a medical examination questionnaire.

The machine learning model (361) of FIG. 3A may be generated in accordance with the flowchart depicted in FIG. 3B.

With reference to FIG. 3B, a system starts the process for training the machine learning model in training, step 371. In steps 372 to 377, one set of training data for the machine learning model in training is generated. Accordingly, the steps 372 to 377 are repeated to generate one or more sets of training data.

In step 372, a user device reads an electronic document and displays one or more questions, in the electronic document, on a display associated with the user device.

A user may input answers to the questions, using a keyboard, a virtual keyboard or a mouse, by touching the display or by speaking the answer on a microphone.

In step 373, the user device receives the answers to the questions from the user and collects information on answering which was generated by an answer operation by the user during inputting or reviewing the answers.

The user device may generate, from the information to the answers, answer history information for the user's answers. Alternatively, the system may generate answer history information for the user's answers from the information for the answers which are obtained from the user device.

In step 374, the system reads, into a memory, the user's answers to the questions and the answer history information for the answers.

In step 375, the system inputs, into the machine learning model in training, the user's answers to the questions and the answer history information for the answers to output an analysis result.

In step 376, the system provides the questions to the answers to the device which presents the questions to the answers to the person who judges the answers to the questions. This person may be a subject matter expert such as a medical professional. The subject matter expert may see the questions to the answers and input an appropriate result, or answer, to the device. The device may send the subject matter expert's result, which was obtained by manually judging the answers to the questions, to the system, which receives the subject matter expert's result and regards same as correct data, or correct answers, for the first machine learning model in training, and for analyzing the answers to the questions.

In step 377, the system may associate the analysis result with the result which was obtained by manually judging the answers to the questions.

In step 378, the system, or another system, inputs into the machine learning model in training, the set of training data (i.e. the answers to the questions, the answer history information for the answers, the analysis result, and, if exists, the result which was obtained by manually judging the answers to the questions to train the machine learning model in training) for example, by adjusting parameters, such as weights and/or bias in hidden layers, in the machine learning model in training so that an output of the machine learning model in training generates correct data.

In step 379, the system, or another system, terminates the process mentioned above.

Referring back to FIG. 3A, the system (301) starts the process of analyzing answers to questions in an electronic document, using the trained machine learning model obtained by the process described in FIG. 3B. The system (301) reads, into a memory, the user's answers and answer history information for the user's answers from a storage where the user's answers and answer history information for the user's answers are stored. The system (301) may read the user's answers to the questions and the answer history information for the user's answers simultaneously or separately.

The embodiment of the answer history information for the user's answers may comprise, for example, but not limited to, information on an answering order of questions, information on the time required for answering the question, information on the number of times or frequency that the answer to the question was changed, biometric information on the user's action, sensor information on the user's action, or a combination thereof.

The system (301) inputs (313) the user's answers to the questions and the answer history information for the user's answers into the machine learning model (361) to output (314) an analysis result. The system (301) obtains the analysis result from the machine learning model (361).

The analysis result may comprise a list of one or more items (or results) having the degree of confidence for each listed item.

The system (301) may select one or more items having a predetermined threshold in the analysis result.

The system (301) may send (315) the analysis result, or the selected one or more items, to the device (332).

The device (332) may receive the analysis result, or the selected one or more items, and then present the analysis result, or the selected one or more items, to the person (352).

The person (352) may see the analysis result, or the selected one or more items, and, optionally, modify (316) the analysis result, or the selected one or more items, if she or he thinks that the analysis result, or the selected one or more items, are inappropriate.

If the device (332) receives the result which was obtained by manually judging the answers to the questions from the person (352), the device (332) may send (317), to the system (301), the result which was obtained by manually judging the answers to the questions.

In one embodiment, the system (301) may store the result which was obtained by manually judging the answers to the questions together with the user's answers to the questions, the answer history information for the user's answers and the analysis result. In this case, a set of the user's answers to the questions, the answer history information for the user's answers, the analysis result, and the result which was obtained by manually judging the answers to the questions may be used to train the machine learning model (361).

In another embodiment, the system (301) may replace the analysis result, or the selected one or more items, with the result which was obtained by manually judging the answers to the questions, if the system (301) receives the result which was obtained by manually judging the answers to the questions from the device (332). In this case, a set of the user's answers to the questions, the answer history information for the user's answers, and the analysis result after the replacement may be used to train the machine learning model (361).

According to the embodiment described in FIG. 3A, the answer history information for the user's answers can be used to obtain an analysis result from the machine learning model (361). The answer history information for the user's answers may be a matter to be considered in order to output an appropriate analysis result.

Therefore, according to the embodiment described in FIG. 3A, the answer history information of the use is reflected to obtain the analysis result.

In a case where the electronic document is a medical interview questionnaire or a medical examination questionnaire, the analysis result may comprise a list of a disease name, a diagnosis and treatment department name, a hospital name, a medicine name, a medical treatment plan, a medical certificate, an inspection name, a medical personnel name such as a doctor name, a nurse name, a laboratory technician name, a pharmacist name, or a combination thereof. The user may be a patient (351). The person (352) may be a medical professional. The medical professional, such as a doctor, may modify the analysis result listed above. Accordingly, a more advisable analysis result can be obtained with the machine learning model (361) which was trained using the answer history information for the answers. Further, the machine learning model (361) may be optionally trained with the answer history information for the user's answers to the questions.

FIG. 4A depicts a flowchart, using a first machine learning model and a second machine learning model, for analyzing answers to questions in an electronic document, in accordance with an embodiment of the present invention.

In the embodiment described in FIG. 4A, a first machine learning model (461) and a second machine learning model (462) each are, in advance, prepared and trained according to the embodiment described in FIGS. 4B and 4C, respectively. The embodiment described in FIGS. 4B and 4C will be first explained below.

The first machine learning model (461) may be a model which is trained using one or more sets of training data, for example, by adjusting parameters, such as weights and/or bias in hidden layers, in the first machine learning model so that an output of the first machine learning model generates correct data. Each set of training data may comprise the following (4-a-i), (4-a-ii) and (4-a-iii): (4-a-i) answers to the questions, where (4-a-i) is an input of the first machine learning model (461); (4-a-ii) a first analysis result which was output by inputting the answers to the questions, into the first machine learning model in training; and (4-a-iii) a result which was obtained by manually judging the answers to the questions. This manually obtained result is regarded as correct data, or correct answers, for analyzing the answers to the questions. In a case where (4-a-iii) the manually obtained result does not exist, (4-a-ii) the first analysis result may be manually acknowledged, or authorized, as a correct data or correct answers. The embodiment of the answer history information for the answers may correspond to that of the aforementioned answer history information for the user's answers. The aforesaid first analysis result may comprise a list of a disease name, in a case where the electronic document is a medical interview questionnaire or a medical examination questionnaire. Further, in a case where the medical interview questionnaire or a medical examination questionnaire is associated with a diagnosis and treatment department name, a hospital name, a medicine name, a medical treatment plan, a medical certificate, an inspection name, a medical personnel name, or a combination thereof, the aforesaid first analysis result may comprise a diagnosis and treatment department name, a hospital name, a medicine name, a medical treatment plan, a medical certificate, an inspection name, a medical personnel name, or a combination thereof. This first analysis result can be obtained, in advance, from a medical record associated with a medical interview questionnaire or a medical examination questionnaire.

The first machine learning model (461) may be generated in accordance with the embodiment depicted in the flowchart of FIG. 4B.

With reference now to FIG. 4B, a system starts the process for training the first machine learning model in training, step 471. In steps 472 to 477, one set of training data for the first machine learning model in training is generated. Accordingly, the steps 472 to 477 are repeated to generate additional sets of training data.

In step 472, a user device reads an electronic document and then displays one or more questions in the electronic document on a display associated with the user device.

A user may input answers to the questions, using a keyboard, a virtual keyboard or a mouse, by touching the display or by speaking the answer on a microphone.

In step 473, the user device receives the answers to the questions from the user and collects information on answering which was generated by an answer operation by the user during inputting or reviewing the answers.

The user device may generate, from the information of the answers, answer history information for the answers. Alternatively, the system may generate answer history information for the answers from the information for the answers which were obtained from the user device.

In step 474, the system reads the answers to the questions into a memory.

In step 475, the system inputs the answers to the questions into the first machine learning model in training to the questions to output a first analysis result.

In step 476, the system provides the questions to the answers to the device which presents the questions to the answers to the person who judges the answers to the questions (e.g. a subject matter expert). The person may see the questions to the answers and then input an appropriate result to the device. The device may send this result, which was obtained by manually judging the answers to the questions, to the system. The system then receives the result which was obtained by manually judging the answers to the questions. This manually obtained result is regarded as correct data, or correct answers, of the first machine learning model in training and of the analyzing the answers to the questions.

In step 477, the system may associate the first analysis result with the result which was obtained by manually judging the answers to the questions.

In step 478, the system, or another system, inputs into the first machine learning model in training, the set of training data (i.e. the answers to the questions, the first analysis result or, if exists, the result which was obtained by manually judging the answers to the questions) to train the first machine learning model in training, for example, by adjusting parameters, such as weights and/or bias in hidden layers, in the first machine learning model in training so that an output of the first machine learning model in training becomes correct data.

In step 479, the system, or another system, terminates the process mentioned above.

The second machine learning model (462) may be generated in accordance with the embodiment depicted in the flowchart of FIG. 4C.

The second machine learning model (462) may be a model which was trained using one or more sets of training data, for example, by adjusting parameters, such as weights and/or bias in hidden layers, in the second machine learning model so that an output of the second machine learning model becomes correct data. Each set of training data may comprise the following (4-b-i), (4-b-ii), (4-b-iii), (4-b-iv) and (4-b-v): (4-b-i) answers to the questions; (4-b-ii) answer history information for the answers; (4-b-iii) a second analysis result which was output by inputting, into the first machine learning model (461), the following (4-b'-i) and (4-b'-ii): (4-b'-i) answers to the questions and (4-b'-ii) answer history information for the answers, where all of (4-b'-i) and (4-b'-ii) are an input of the second machine learning model (462); (4-b-iv) a second analysis result which is an output of the second machine learning model (462); and (4-b-v) a final result which is obtained by manually judging the answers to the questions. This manually obtained final result is regarded as correct data, or correct answers, of analyzing the answers to the questions. In a case where (4-b-v) the manually obtained final result does not exist, (4-b-iii) the second analysis result may be manually acknowledged, or authorized, as correct data, or correct answers.

The embodiment of the answer history information for the answers corresponds to that of the above-mentioned answer history information for the user's answers. The aforesaid second analysis result may comprise a list of a disease name, in a case where the electronic document is a medical interview questionnaire or a medical examination questionnaire. Further, in a case where the medical interview questionnaire or the medical examination questionnaire is associated with a diagnosis and treatment department name, a hospital name, a medicine name, a medical treatment plan, a medical certificate, an inspection name, a medical personnel name, or a combination thereof, the aforesaid second analysis result may comprise a diagnosis and treatment department name, a hospital name, a medicine name, a medical treatment plan, a medical certificate, an inspection name, a medical personnel name, or a combination thereof. This second analysis result may be obtained, in advance, from a medical record associated with a medical interview questionnaire or a medical examination questionnaire.

The second learning model (462) may be generated in accordance with the embodiment depicted in the flowchart of FIG. 4C.

With reference to FIG. 4C, the system starts the process for training the second machine learning model in training, step 491. In steps 492 to 495, one set of training data for the second machine learning model in training is generated. Accordingly, the steps 492 to 495 are repeated to generate additional sets of training data.

In step 492, the system reads, in to a memory, the answers to the questions, the answer history information for the answers, and the first analysis result or, if exists, the result which was obtained by manually judging the answers to the questions.

In step 493, the system inputs, into the second machine learning model in training, the answers to the questions, the answer history information for the answers, and the first analysis result or, if exists, the result which was obtained by manually judging the answers to the questions to output a second analysis result.

In step 494, the system provides the questions to the answers, to the device which presents the questions to the answers, to the person who manually judges the answers to the questions. The person (e.g. subject matter expert) may see the questions to the answers, and optionally, provide further information relating to the answers and input an appropriate result to the device. The device may send this result, which was obtained by manually judging the answers to the questions, to the system. The system then receives the final result which was obtained by manually judging the answers to the questions. This manually obtained final result is regarded as a correct data, or correct answers, of the second machine learning model in training and of the analyzing the answers to the questions.

In step 495, the system may associate the second analysis result or, if exists, the result which was obtained by manually judging the answers to the questions with the final result which was obtained by manually judging the answers to the questions.

In step 496, the system, or another system, inputs into the second machine learning model in training, the set of training data, i.e. the answers to the questions, the answer history information on the answers, and the first analysis result or, if exists, the result which was obtained by manually judging the answers to the questions and the second analysis result or, if exists, the final result which was obtained by manually judging the answers to the questions to train the second machine learning model in training, for example, by adjusting parameters, such as weights and/or bias in hidden layers, in the second machine learning model in training so that an output of the second machine learning model in training becomes a correct data.

In step 497, the system, or another system, terminates the process mentioned above.

Referring back to FIG. 4A, the system (401) starts the process of analyzing answers to questions in an electronic document, using the trained first machine learning model and the trained second machine learning model, which were obtained by the process described in FIGS. 4B and 4C, respectively. The system (401) reads, into a memory, the user's answers to the questions and answer history information for the user's answers from a storage where the user's answers to the questions and answer history information for the user's answers are stored. The system (401) may read the user's answers to the questions and the answer history information for the user's answers simultaneously or separately.

The embodiment of the answer history information for the user's answers may comprise, for example, but not limited to, information on an answering order of questions, information on the time required for answering the question, information on the number of times or frequency that the answer to the question was changed, biometric information for the user's action, sensor information for the user's action, or a combination thereof.

The system (401) inputs (413) the user's answer to the questions into the first machine learning model (461) to output (414) a first analysis result. The system (401) obtains the first analysis result from the first machine learning model (461).

The first analysis result may comprise a list of one or more items (or results) having the degree of confidence for each listed item.

The system (401) may select one or more items having a predetermined threshold in the first analysis result.

The system (401) may send (415) the first analysis result or the selected one or more items to the device (432).

The device (432) may receive the first analysis result, or the selected one or more items, and present the first analysis result, or the selected one or more items, to the person (452).

The person (452) may see the first analysis result, or the selected one or more items, and, optionally, modify (416) the first analysis result, or the selected one or more items, if she or he thinks that the first analysis result, or the selected one or more items, are inappropriate.

If the device (432) receives the result which was obtained by manually judging the answers to the questions from the person (452), the device (432) may send (417), to the system (401), the result which was obtained by manually judging the answers to the questions.

In one embodiment, if the system (401) does not receive the result which was obtained by manually judging the answers to the questions from the device (432), the system (401) may input (418), into the second machine learning model (462), the user's answers to the questions, the answer history information for the user's answers, and the first analysis result to output (419) a second analysis result. The system (401) obtains the second analysis result from the second machine learning model (462).

In another embodiment, if the system (401) receives the result which was obtained by manually judging the answers to the questions from the device (432), the system (401) may input (418), into the second machine learning model (462), the user's answers to the questions, the answer history information for the user's answers, the first analysis result, and the result which was obtained by manually judging the answers to the questions to output (419) a second analysis result. The system (401) obtains the second analysis result from the second machine learning model (462).

In another embodiment, if the system (401) receives the result which was obtained by manually judging the answers to the questions from the device (432), the system (401) may replace the first analysis result, or the selected one or more items, with the result which was obtained by manually judging the answers to the questions. The system (401) may input (418), into the second machine learning model (462), the user's answers to the questions, the answer history information on the user's answers, and the first analysis result after the replacement to output (419) a second analysis result. The system (401) obtains the second analysis result from the second machine learning model (462).

In the above-mentioned embodiment, the following second machine learning model (462) may be used: the second machine learning model (462) to be used is trained further using content obtained by inputting, into the first machine learning model (461), answers to the questions, and the answer history information for the answers, to output an analysis result and then modifying the output analysis result.

The second analysis result may comprise a list of one or more items (or results) having the degree of confidence for each listed item.

The system (401) may select one or more items having a predetermined threshold in the second analysis result.

The system (401) may send (420) the second analysis result or the selected one or more items to the device (432).

The device (432) may receive the second analysis result or the selected one or more items and then present the second analysis result or the selected one or more items to the person (452).

The person (452) may see the second analysis result or the selected one or more items.

According to the embodiment described in FIG. 4A, the answer history information for the user's answers may be used to obtain a second analysis result from the second machine learning model (462). The answer history information for the user's answers may be a matter to be considered in order to output an appropriate second analysis result.

Therefore, according to the embodiment described in FIG. 4A, the answer history information of the use is reflected to obtain the second analysis result.

In a case where the electronic document is a medical interview questionnaire or a medical examination questionnaire, each of the first and second analysis results may comprise a list of a disease name, a diagnosis and treatment department name, a hospital name, a medicine name, a medical treatment plan, a medical certificate, an inspection name, a medical personnel name such as a doctor name, a nurse name, a laboratory technician or a pharmacist name, or a combination thereof. The user may be a patient (451). The person (452) may be a medical professional. The medical professional, such as a doctor, may modify the first analysis result listed above. Accordingly, a more advisable analysis result (i.e. a second analysis result) can be obtained with the first machine learning model (461) and the second machine learning model (462) which was trained using the answer history information for the answers. Further, the second machine learning model (462) may be optionally trained with the answer history information for the user's answers.

FIG. 5A depicts another flowchart, using a first machine learning model and a second machine learning model, for analyzing answers to questions in an electronic document, in accordance with an embodiment of the present invention.

In the embodiment described in FIG. 5A, a first machine learning model (561) and a second machine learning model (562) each are in advance prepared and trained according to the embodiments described in FIGS. 5B and 5C, respectively. The embodiments described in FIGS. 5B and 5C will be first explained below.

The first machine learning model (561) may be a model which was trained using one or more sets of training data, for example, by adjusting parameters, such as weights and/or bias in hidden layers, in the first machine learning model so that an output of the first machine learning model becomes correct data. Each set of training data may comprise the following (5-a-i), (5-a-ii), (5-a-iii) and (5-a-iv): (5-a-i) answers to the questions, where (5-a-i) is an input of the first machine learning model (561); (5-a-ii) answer history information on the answers; and (5-a-iii) a first analysis result which was output by inputting the following (5-a'-i), (5-a'-ii) and (5-a'-iii) into the first machine learning model in training: (5-a'-i) answers to the questions and (5-a'-ii) answer history information on the answers, where all of (5-a'-i) and (5-a'-ii) are an input of the first machine learning mode; and (5-a'-iii) a first analysis result which was output by inputting, the answers to the question and answer history information for the answers into the first machine learning model in training; and (5-a-iv) a result which was obtained by manually judging the answers to the questions. This manually obtained result is regarded as a correct data, or correct answer, for analyzing the answers to the questions. In a case where (5-a-iv) the manually obtained result does not exist, (5-a-iii) the first analysis result may be manually acknowledged, or authorized, as a correct data or correct answer.

The embodiment of the answer history information for the answers may correspond to that of the aforementioned answer history information for the user's answers to the questions. The aforesaid first analysis result may comprise a list of a disease name, in a case where the electronic document is a medical interview questionnaire or a medical examination questionnaire. Further, in a case where the medical interview questionnaire or the medical examination questionnaire is associated with a diagnosis and treatment department name, a hospital name, a medicine name, a medical treatment plan, a medical certificate, an inspection name, a medical personnel name, or a combination thereof, the aforesaid first analysis result may comprise a diagnosis and treatment department name, a hospital name, a medicine name, a medical treatment plan, a medical certificate, an inspection name, a medical personnel name, or a combination thereof. This first analysis result may be obtained in advance from a medical record associated with a medical interview questionnaire or a medical examination questionnaire.

The first machine learning model (561) may be generated in accordance with the embodiment depicted in the flowchart of FIG. 5B.

With reference to FIG. 5B, a system starts the process for training the first machine learning model in training, step 571. In steps 572 to 577, one set of training data for the first machine learning model in training is generated. Accordingly, the steps 572 to 577 are repeated to generate additional sets of training data.

In step 572, a user device reads an electronic document and then displays one or more questions in the electronic document on a display associated with the user device.

A user may input answers to the questions, using a keyboard, a virtual keyboard or a mouse, by touching the display or by speaking the answer on a microphone.

In step 573, the user device receives the answers to the questions from the user and collects information on answering which was generated by an answer operation by the user during inputting or reviewing the answers.

The user device may generate, from the information on the answers, answer history information for the answers. Alternatively, the system may generate answer history information for the answers from the information for the answers which were obtained from the user device.

In step 574, the system reads the answers to the questions and answer history information for the answers into a memory.

In step 575, the system inputs the answers and answer history information for the answers into the first machine learning model in training to the questions to output a first analysis result.

In step 576, the system provides the questions to the answers, to the device which presents the questions to the answers, to the person who judges the answers to the questions (i.e. a subject matter expert). The person may see the questions to the answers and then input an appropriate result to the device. The device sends this result, which was obtained by manually judging the answers to the questions, to the system. The system receives the result which was obtained by manually judging the answers to the questions. This manually obtained result is regarded as a correct data, or correct answers, of the first machine learning model in training and of the analyzing the answers to the questions.

In step 577, the system may associate the first analysis result with the result which was obtained by manually judging the answers to the questions.

In step 578, the system, or another system, inputs into the first machine learning model in training, the set of training data, i.e. the answers to the questions, the answer history information on the answers, the first analysis result or, if exists, the result which was obtained by manually judging the answers to the questions to train the first machine learning model in training, for example, by adjusting parameters, such as weights and/or bias in hidden layers, in the machine learning model in training so that an output of the first machine learning model in training becomes a correct data.

In step 579, the system, or another system, terminates the process mentioned above.

The second machine learning model (462) may be generated in accordance with the embodiment depicted in the flowchart of FIG. 5C.

The second machine learning model (562) may be a model which was trained using one or more sets of training data, for example, by adjusting parameters, such as weights and/or bias in hidden layers, in the second machine learning model so that an output of the second machine learning model generates correct data. Each training data may comprise the following (5-b-i), (5-b-ii), (5-b-iii), (5-b-iv) and (5-b-v): (5-b-i) answers to the questions, (5-b-ii) answer history information for the answers, and (5-b-iii) a second analysis result which was output by inputting, into the first machine learning model (561), the following (5-b'-i) and (5-b'-ii): (5-b'-i) answers to the questions and (5-b'-ii) answer history information for the answers, where all of (5-b'-i) and (5-b'-ii) are an input of the second machine learning model (562); (5-b-iv) a second analysis result which is an output of the second machine learning model (562); and (5-b-v) a final result which was obtained by manually judging the answers to the questions. This manually obtained final result is regarded as a correct data, or correct answers, for analyzing the answers to the questions. In a case where (5-b-v) the manually obtained final result does not exist, (5-b-iii) the second analysis result may be manually acknowledged, or authorized, as correct data or correct answers. The embodiment of the answer history information for the answers corresponds to that of the above-mentioned answer history information for the user's answers to the questions. The aforesaid second analysis result may comprise a list of a disease name, in a case where the electronic document is a medical interview questionnaire or a medical examination questionnaire. Further, in a case where the medical interview questionnaire or the medical examination questionnaire is associated with a diagnosis and treatment department name, a hospital name, a medicine name, a medical treatment plan, a medical certificate, an inspection name, a medical personnel name, or a combination thereof, the aforesaid second analysis result may comprise a diagnosis and treatment department name, a hospital name, a medicine name, a medical treatment plan, a medical certificate, an inspection name, a medical personnel name, or a combination thereof, in a case where the electronic document is a medical interview questionnaire or a medical examination questionnaire. This second analysis result may be obtained in advance from a medical record associated with a medical interview questionnaire or a medical examination questionnaire.

The second learning model (562) may be generated in accordance with the embodiment depicted in the flowchart of FIG. 5C.

With reference to FIG. 5C, the system starts the process for training the second machine learning model in training, step 591. In steps 592 to 595, one set of training data for the second machine learning model in training is generated. Accordingly, the steps 592 to 595 are repeated to generate additional sets of training data.

In step 592, the system reads, in to a memory, the answers to the questions, the answer history information on the answers, and the first analysis result or, if exists, the result which was obtained by manually judging the answers to the questions.

In step 593, the system inputs, into the second machine learning model in training, the answers to the questions, the answer history information for the answers, and the first analysis result or, if exists, the result which was obtained by manually judging the answers to the questions to output a second analysis result.

In step 594, the system provides the questions to the answers to the device which presents the questions to the answers to the person who judges the answers to the questions (i.e. a subject matter expert). The person may see the questions to the answers, and optionally further information relating to the answers, and then inputs an appropriate result to the device. Then, the device sends this result which was obtained by manually judging the answers to the questions. The system then receives the final result which was obtained by manually judging the answers to the questions. This manually obtained final analysis result is regarded as a correct data or correct answer of the second machine learning model in training and of the analyzing the answers to the questions.

In step 595, the system may associate the second analysis result or, if exists, the result which was obtained by manually judging the answers to the questions with the final result which was obtained by manually judging the answers to the questions.

In step 596, the system or another system inputs, into the second machine learning model in training, the set of training data, i.e. the answers to the questions, the answer history information on the answers, and the first analysis result or, if exists, the result which was obtained by manually judging the answers to the questions and the second analysis result or, if exists, the final result which was obtained by manually judging the answers to the questions to train the second machine learning model in training, for example, by adjusting parameters, such as weights and/or bias in hidden layers, in the second machine learning model in training so that an output of the second machine learning model in training becomes correct data.

In step 597, the system, or another system, terminates the process mentioned above.

Referring back to FIG. 5A, the system (501) starts the process of analyzing answers to questions in an electronic document, using the trained first machine learning model and the trained second machine learning model which were obtained by the process described in FIGS. 4B and 4C, respectively. The system (501) reads, into a memory, the user's answers to the questions and answer history information for the user's answers from a storage where the user's answers to the questions and answer history information for the user's answers are stored. The system (501) may read the user's answers to the questions and the answer history information for the user's answers simultaneously or separately.

The embodiment of the answer history information for the user's answers may comprise, for example, but not limited to, information on an answering order of questions, information on the time required for answering the question, information on the number of times or frequency that the answer to the question was changed, biometric information on the user's action, sensor information on the user, or a combination thereof.

The system (501) inputs (513), into the first machine learning model (561), the user's answers to the questions and the answer history information for the user's answers to output (514) a first analysis result. The system (501) obtains the first analysis result from the first machine learning model (561).

The first analysis result may comprise a list of one or more items (or results) having the degree of confidence for each listed item.

The system (501) may select one or more items having a predetermined threshold in the first analysis result.

The system (501) may send (515) the first analysis result or the selected one or more items to the device (532).

The device (532) may receive the first analysis result or the selected one or more items and then present the first analysis result or the selected one or more items to the person (552).

The person (552) may see the first analysis result or the selected one or more items and, optionally, modify (516) the first analysis result or the selected one or more items, if she or he thinks that the first analysis result or the selected one or more items is inappropriate.

If the device (532) receives the result which was obtained by manually judging the answers to the questions from the person (552), the device (532) may send (517), to the system (501), the result which was obtained by manually judging the answers to the questions.

In one embodiment, if the system (501) does not receive the result which was obtained by manually judging the answers to the questions from the device (532), the system (501) may input (518), into the second machine learning model (562), the user's answers, the answer history information for the user's answers, and the first analysis result to output (519) a second analysis result. The system (501) obtains the second analysis result from the second machine learning model (562).

In another embodiment, if the system (501) receives the result which was obtained by manually judging the answers to the questions from the device (532), the system (501) may input (518), into the second machine learning model (562), the user's answers, the answer history information from the user's answers, the first analysis result, and the result which was obtained by manually judging the answers to the questions to output (519) a second analysis result. The system (501) obtains the second analysis result from the second machine learning model (562).

In another embodiment, if the system (501) receives the result which was obtained by manually judging the answers to the questions from the device (532), the system (501) may replace the first analysis result, or the selected one or more items, with the result which was obtained by manually judging the answers to the questions, if the system (501) receives the result which was obtained by manually judging the answers to the questions from the device (532). The system (501) may input (518), into the second machine learning model (562), the user's answers, the answer history information from the user's answers, and the first analysis result after the replacement to output (519) a second analysis result. The system (501) obtains the second analysis result from the second machine learning model (562).

In the above-mentioned embodiment, the following second machine learning model (562) may be used: the second machine learning model (562) to be used is trained further using content obtained by inputting, into the first machine learning model (561), answers to the questions, and the answer history information for the answers, to output an analysis result and then modifying the output analysis result.

The second analysis result may comprise a list of one or more items (or results) having the degree of confidence for each listed item.

The system (501) may select one or more items having a predetermined threshold in the second analysis result.

The system (501) may send (520) the second analysis result or the selected one or more items to the device (532).

The device (532) may receive the second analysis result, or the selected one or more items, and then present the second analysis result, or the selected one or more items, to the person (552).

The person (552) may see the second analysis result, or the selected one or more items.

According to the embodiment described in FIG. 5A, the answer history information for the user's answers may be used to obtain a first analysis result and a second analysis result from the first machine learning model (562) and the second machine learning model (562), respectively. The answer history information for the user's answers may be a matter to be considered in order to output an appropriate first analysis result and an appropriate second analysis result.

Therefore, according to the embodiment described in FIG. 5A, the answer history information of the user is reflected in order to obtain the first analysis result and the second analysis result.

In a case where the electronic document is a medical interview questionnaire or a medical examination questionnaire, each of the first and second analysis results may comprise a list of a disease name, a diagnosis and treatment department name, a hospital name, a medicine name, a medical treatment plan, a medical certificate, an inspection name, a medical personnel name such as a doctor name, a nurse name, a laboratory technician or a pharmacist name, or a combination thereof. The user may be a patient (551). The person (552) may be a medical professional. The medical professional, such as a doctor, may modify the first analysis result listed above. Accordingly, a more advisable analysis result (i.e. a second analysis result) may be obtained with the first machine learning model (561) and the second machine learning model (562), where both the first machine learning model (561) and the second machine learning model (562) are trained using the answer history information on the answers. Further, the first machine learning model (561) may be optionally trained with the answer history information on the user's answers, and the second machine learning model (562) may be optionally trained with the answer history information on the user's answers.

Figure 6A:
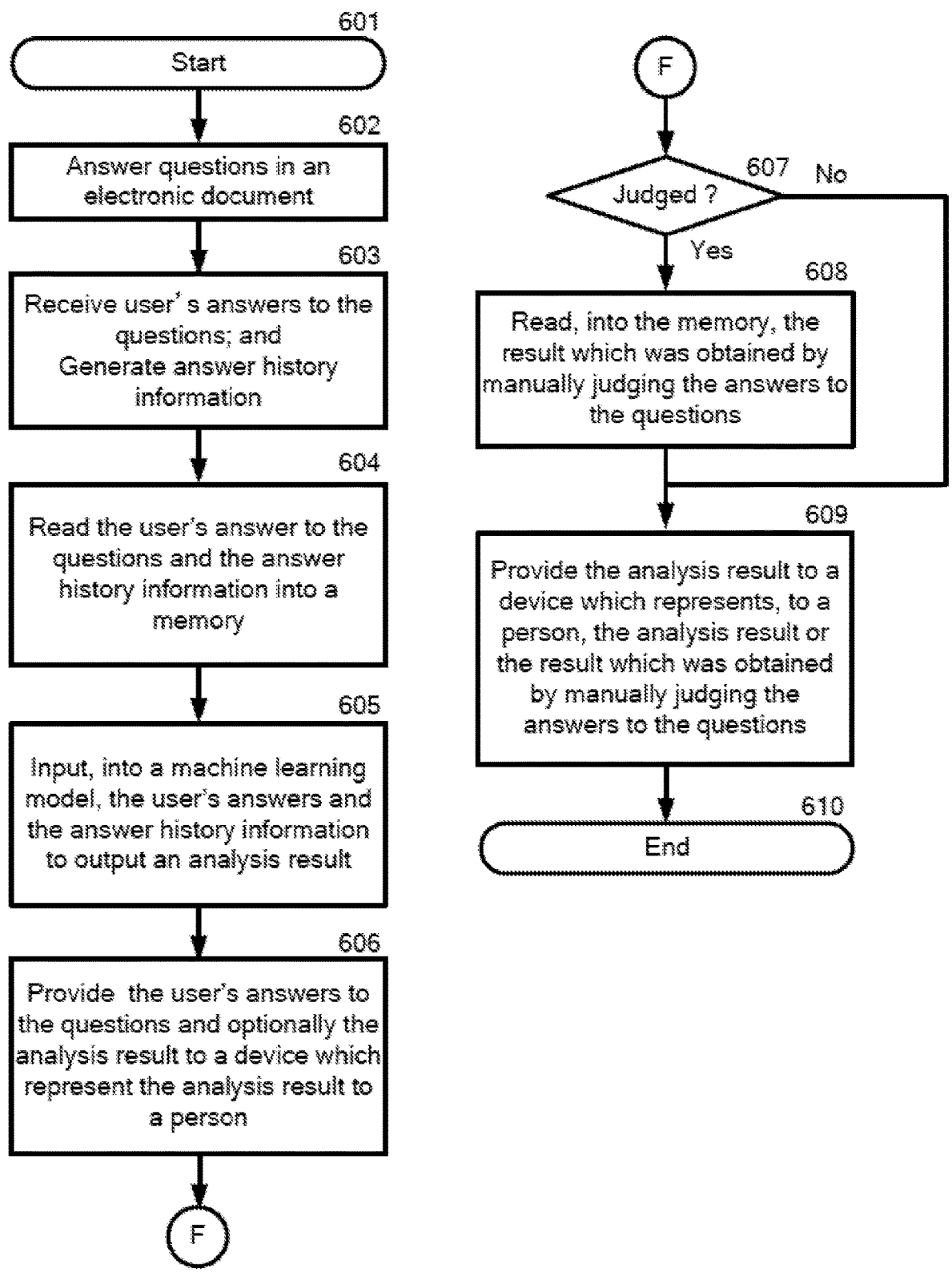
FIGS. 6A and 6B each depict a flowchart for analyzing answers to questions in an electronic document, in accordance with an embodiment of the present invention.
Figure 6B:
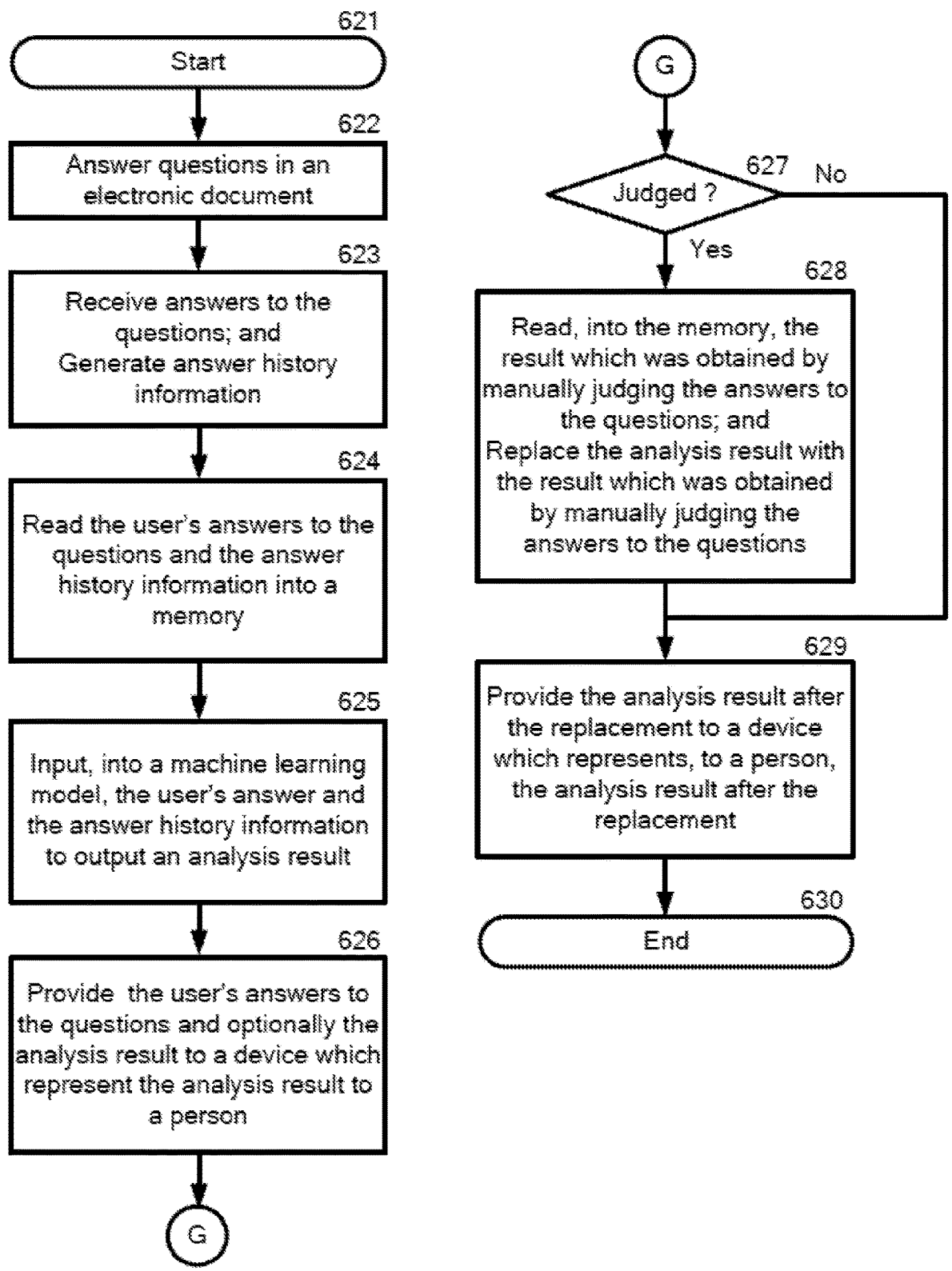

FIGS. 6A and 6B each depict a flowchart for analyzing answers to questions in an electronic document, in accordance with embodiments of the present invention.

FIG. 6A depicts a flowchart corresponding to the embodiment described in FIG. 3A. In the embodiment, the machine learning model (361) described in FIG. 3A is prepared according to the flowchart described in FIG. 3B prior to a start of the process. The answer history information for the user's answers may be used to obtain an analysis result from the machine learning model (361). Further, the result which is obtained by manually judging the answers to the questions, together with the answer history information for the user's answers, may used to be input together with the answer history information for the user's answers to train the machine learning model (361).

In step 601, the system (301) starts the process mentioned above.

In step 602, the user device (331) reads an electronic document and then displays one or more questions in the electronic document on a display associated with the user device (331).

A user may input answers to the questions, using a keyboard, a virtual keyboard or a mouse, by touching the display or by speaking the answer on a microphone.

In step 603, the user device (331) receives the user's answers to the questions from the user and collects information on answering which was generated by an answer operation by the user (351) during inputting or reviewing the answers.

The user device (331) may generate, from the information on the answers, answer history information for the user's answers. Alternatively, the system (301) may generate answer history information for the user's answers from the information on the answers which were obtained from the user device (331).

In step 604, the system (301) reads, into a memory, the user's answers to the questions and the answer history information for the user's answers.

In step 605, the system (301) inputs, into the machine learning model (361), the user's answers to the questions and the answer history information for the user's answers to output an analysis result.

In an optional step 606, the system (301) may provide the user's answers to the questions and, optionally, the analysis result to the device (332). The device (332) may present the user's answers to the questions, and optionally, the analysis result to the person (352) associated with the device (332).

The person (352) may manually judge the user's answers to the questions and then input a result against the user's answers to the questions, if she or he thinks that the analysis result, or the selected one or more items, is inappropriate.

In an optional step 607, the system (301) may judge whether the result against the user's answers to the questions was input by the aforesaid person (352). If the judgment is positive, the system (301) may proceed to step 608. Meanwhile, if the judgment is negative, the system (301) may proceed to step 609.

In an optional step 608, the system (301), or another system may read, into the memory, the result which was obtained by manually judging the answers to the questions.

In an optional step 609, the system (301), or another system, may provide the analysis result to a device which represents, to a person, the analysis result or the result which was obtained by manually judging the answers to the questions.

In step 610, the system, or another system, terminates the process mentioned above.

The system (301) may provide the training data set obtained from the system (301) to a system where the training of the machine learning model (361) is performed according to the process described in FIG. 3B.

FIG. 6B illustrates an embodiment of a flowchart corresponding to the diagram described in FIG. 3A. In the embodiment, the machine learning model (361) described in FIG. 3A is prepared according to the flowchart described in FIG. 3B prior to a start of the process. The answer history information for the user's answers may be used to obtain an analysis result from the machine learning model (361).

Further, the analysis result may be replaced with the result which was obtained by manually judging the answers to the questions and then the analysis result after the replacement can be provided to a user.

In step 621, the system (401) starts the process mentioned above.

Steps 622 to 627 correspond to steps 602 to 607, respectively. Accordingly, the overlapping explanations of steps 622 to 627 are omitted here.

In an optional step 628, the system (301) or another system may read, into the memory, the result which was obtained by manually judging the answers to the questions. The system (301) or another system may then replace the analysis result with the result which was obtained by manually judging the answers to the questions.

In optional step 629, the system (301), or another system, may provide the analysis result to a device which represents, to a person, the analysis result after the replacement.

In step 630, the system, or another system, terminates the process mentioned above.

The system (301) may provide the training data set, obtained from the system (301), to a system where the training of the machine learning model (361) is performed according to the process described in FIG. 3B.

Figure 7A:
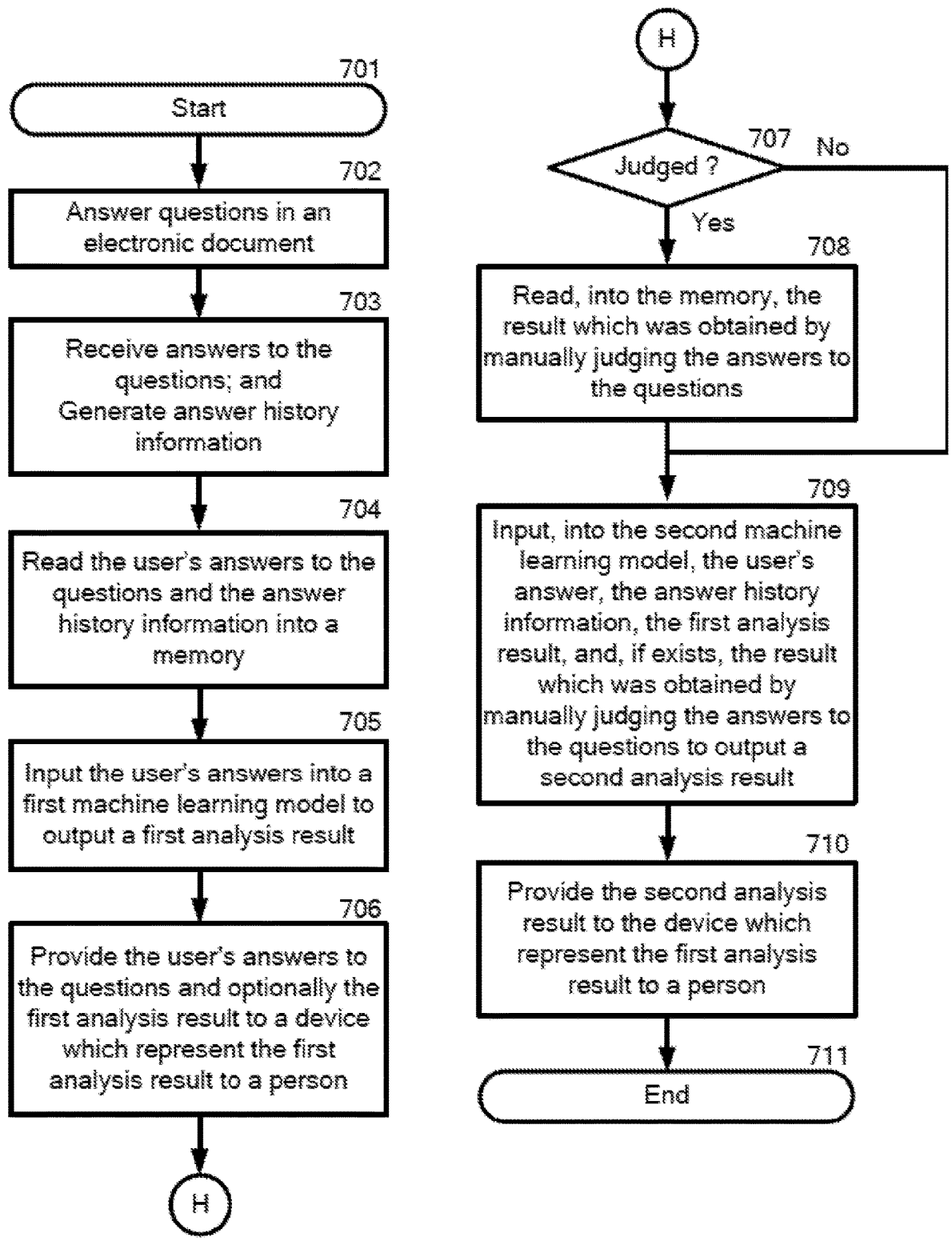
FIGS. 7A and 7B each depict a flowchart for analyzing answers to questions in an electronic document, in accordance with an embodiment of the present invention.
Figure 7B:
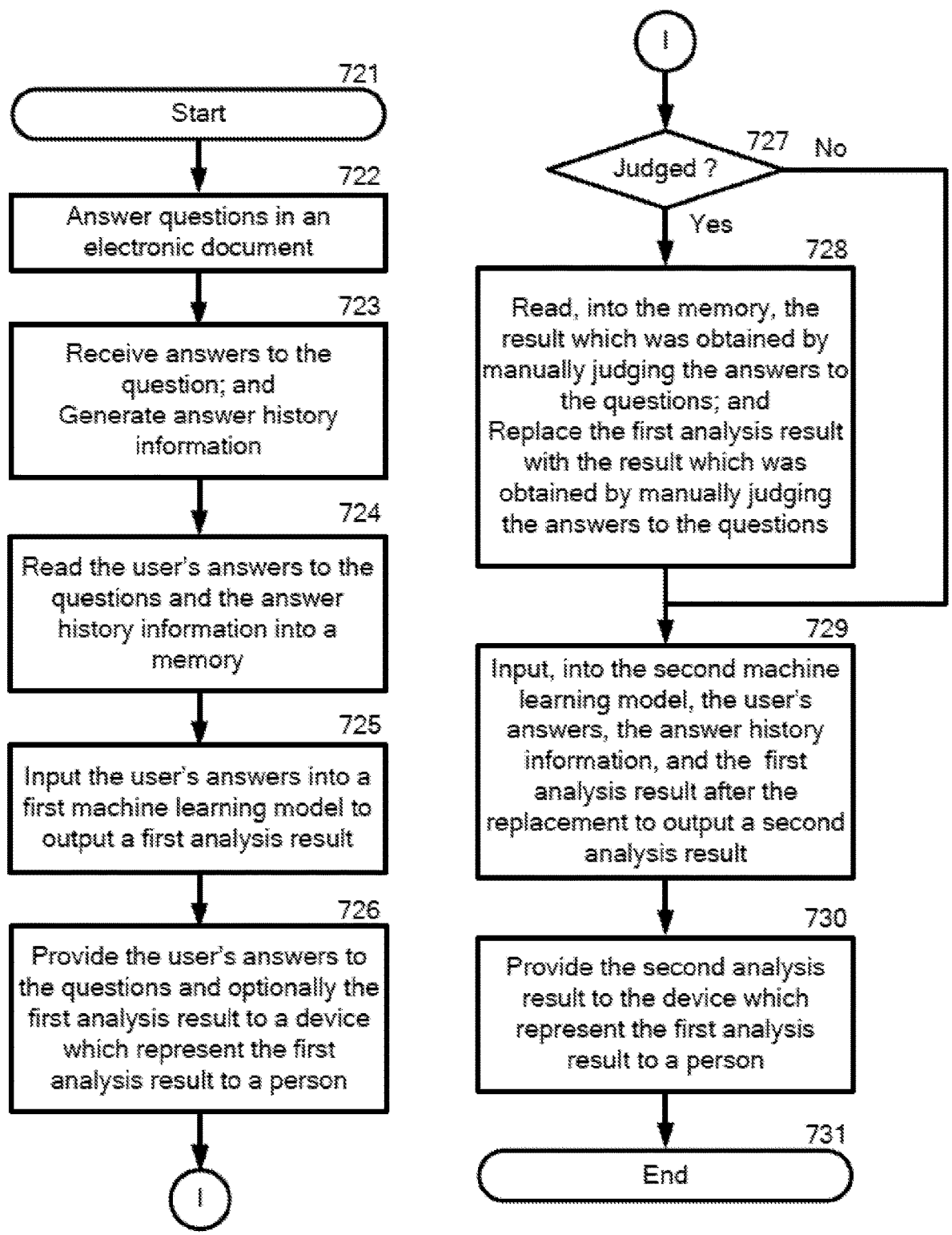

FIGS. 7A and 7B each depict a flowchart for analyzing answers to questions in an electronic document, in accordance with embodiments of the present invention.

FIG. 7A illustrates an embodiment of a flowchart corresponding to the diagram described in FIG. 4A. In the embodiment, the first machine learning model (461) and the second machine learning model (462) described in FIG. 4A are prepared according to the flowcharts described in FIGS. 4B and 4C, respectively, prior to a start of the process. The answer history information for the user's answers may be used to obtain a second analysis result from the second machine learning model (462).

In step 701, the system (401) starts the process mentioned above.

In step 702, the user device (431) reads an electronic document and displays one or more questions in the electronic document on a display associated with the user device (431).

A user may input answers to the questions, using a keyboard, a virtual keyboard or a mouse, by touching the display or by speaking the answer on a microphone.

In step 703, the user device (431) receives the user's answers to the questions from the user and collects information on answering which was generated by an answer operation by the user (451) during inputting or reviewing the answers.

The user device (431) may generate, from the information on the answers, answer history information for the user's answers. Alternatively, the system (401) may generate answer history information for the user's answers from the information on the answers which were obtained from the user device (431).

In step 704, the system (401) reads, into a memory, the user's answers to the questions and the answer history information for the user's answers.

In step 705, the system (401) inputs the user's answer into the first machine learning model (461) to output a first analysis result.

In step 706, the system (401) provides the user's answers to the questions and, optionally, the analysis result to the device (432). The device (432) may present the user's answers to the questions and, optionally, the analysis result to the person (452) associated with the device (432).

The person (452) may manually judge the user's answers to the questions and then input a result against the user's answers to the questions, if she or he thinks that the first analysis result or the selected one or more items are inappropriate.

In step 707, the system (401) may judge whether the result against the user's answers to the questions was input by the aforesaid person (452). If the judgment is positive, the system (401) may proceed to step 708. Meanwhile, if the judgment is negative, the system (401) may proceed to step 709.

In optional step 708, the system (401), or another system, reads into memory the result which was obtained by manually judging the answers to the questions.

In step 709, the system (401) inputs, into the second machine learning model (462), the user's answers, the answer history information for the user's answers, the first analysis result, and, if exists, the result which was obtained by manually judging the answers to the questions to output a second analysis result.

In optional step 710, the system (401), or another system, may provide the second analysis result to a device which represents, to a person, the first analysis result or the result which was obtained by manually judging the answers to the questions.

In step 711, the system terminates the process mentioned above.

The system (401) may provide the training data set obtained from the system (401) to a system where the trainings of the first machine learning model (461) and the second machine learning model (462) are performed according to the process described in FIGS. 4B and 4C, respectively.

FIG. 7B depicts a flowchart embodiment corresponding to the diagram described in FIG. 4A. In the embodiment, the first machine learning model (461) and the second machine learning model (462), described in FIG. 4A, are prepared according to the flowcharts described in FIGS. 4B and 4C, respectively, prior to a start of the process. The answer history information for the user's answers may be used to obtain a second analysis result from the second machine learning model (462). Further, the first analysis result may be replaced with the result which was obtained by manually judging the answers to the questions and then the first analysis result, after the replacement, may be provided to a user.

In step 721, the system (401) starts the process mentioned above.

Steps 722 to 727 correspond to steps 702 to 707, respectively. Accordingly, the overlapping explanations of steps 722 to 727 are omitted here.

In step 728, the system (401) reads, into the memory, the result which was obtained by manually judging the answers to the questions. The system (401), or another system, may then replace the first analysis result with the result which was obtained by manually judging the answers to the questions.

In step 729, the system (401) inputs, into the second machine learning model (462), the user's answers, the answer history information for the user's answers, and the first analysis result after the replacement to output a second analysis result.

In an optional step 730, the system (401), or another system, may provide the second analysis result to a device which represents, to a person, the first analysis result or the result which was obtained by manually judging the answers to the questions.

In step 731, the system terminates the process mentioned above.

The system (401) may provide the training data set obtained from the system (401) to a system where the trainings of the first machine learning model (461) and the second machine learning model (462) are performed according to the process described in FIGS. 4B and 4C, respectively.

Figure 8A:
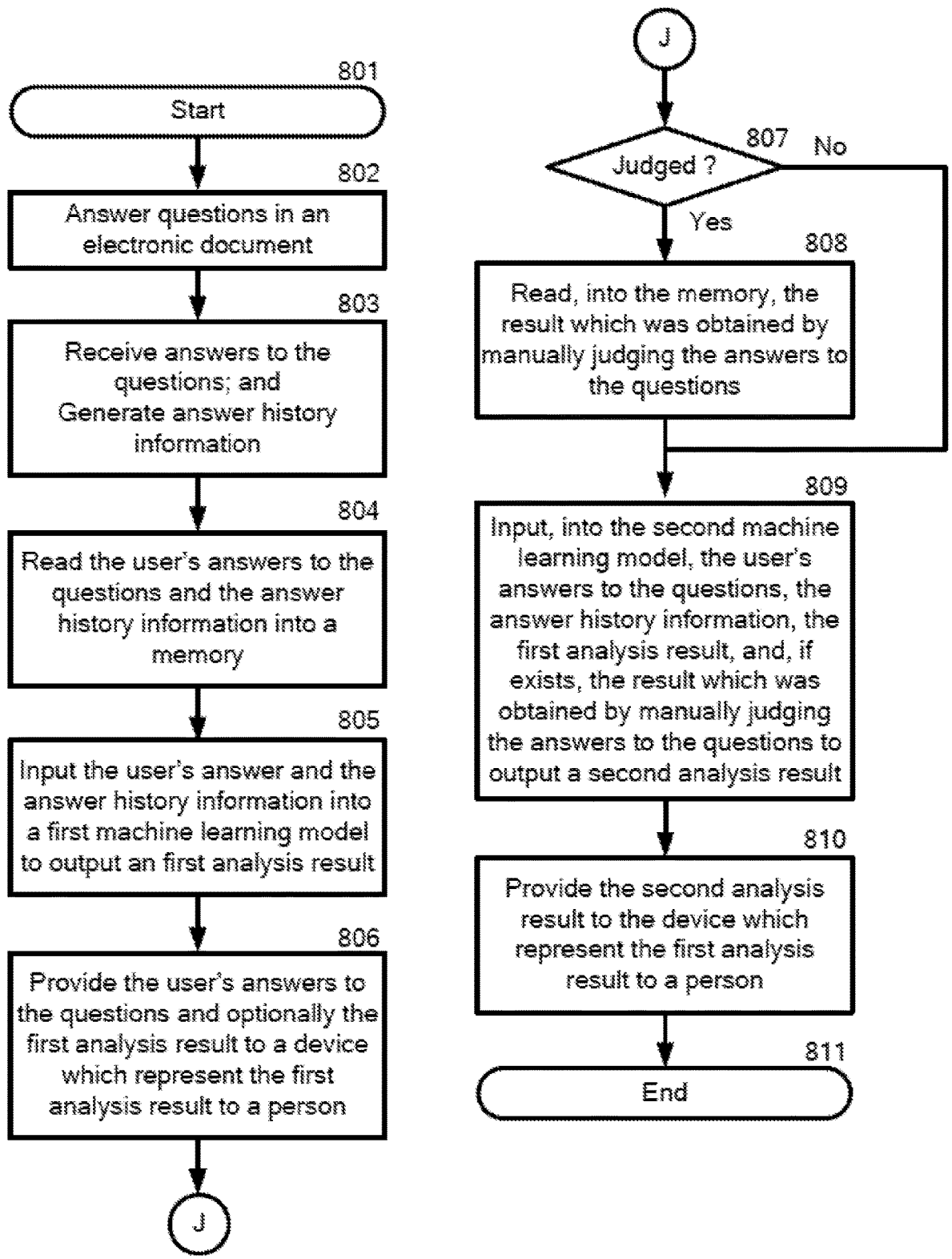
FIGS. 8A and 8B each depict a flowchart for analyzing answers to questions in an electronic document, in accordance with an embodiment of the present invention.
Figure 8B:
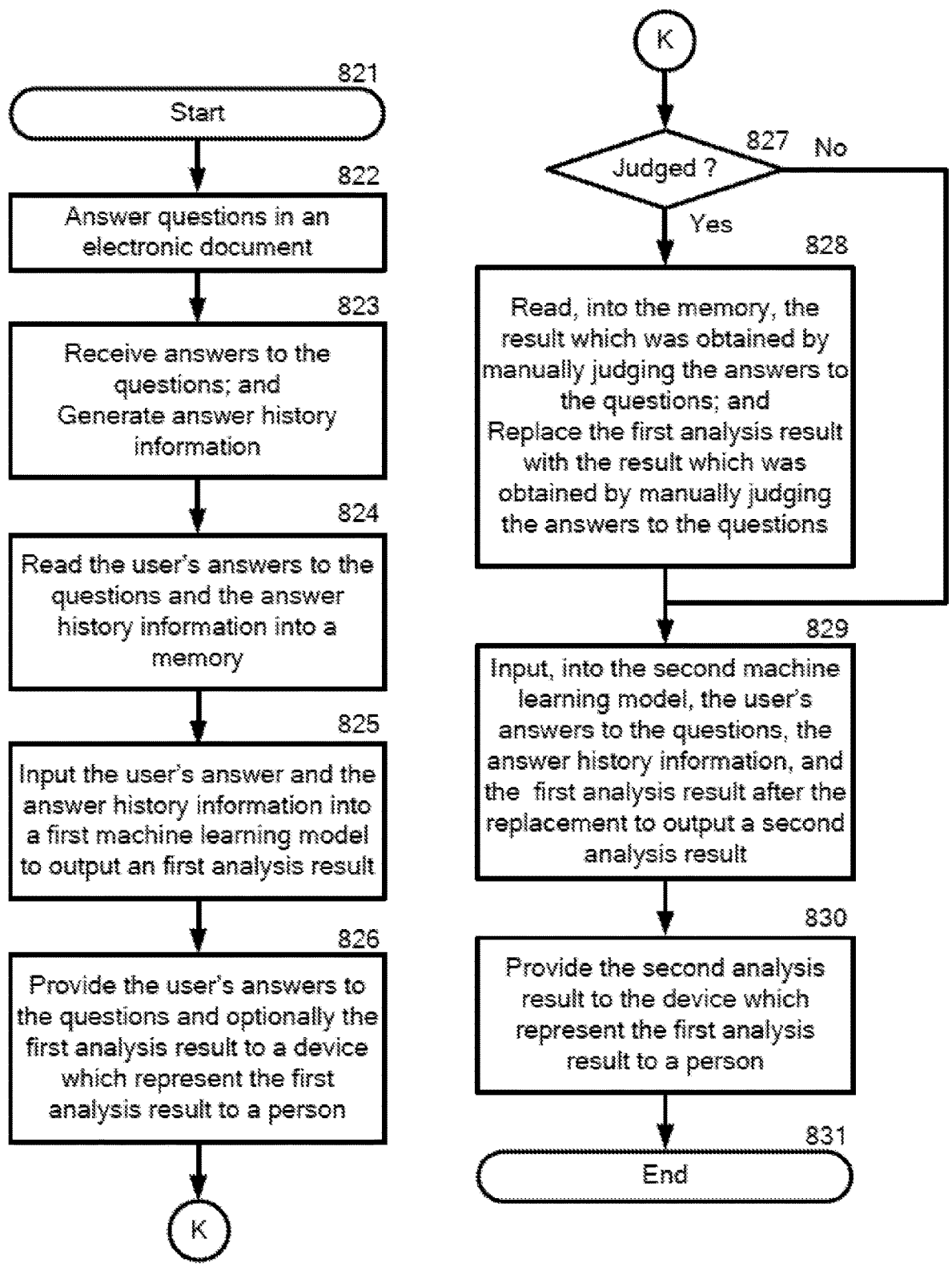

FIGS. 8A and 8B each depict a flowchart for analyzing answers to questions in an electronic document, in accordance with embodiments of the present invention.

FIG. 8A illustrates an embodiment of a flowchart corresponding to the diagram described in FIG. 5A. In the embodiment, the first machine learning model (561) and the second machine learning model (562), described in FIG. 5A, are prepared according to the flowcharts described in FIGS. 5B and 5C, respectively, prior to a start of the process. The answer history information for the user's answers may be used to obtain a first analysis result from the first machine learning model (561) and further, the answer history information for the user's answers may be used to obtain a second analysis result from the second machine learning model (562).

In step 801, the system (501) starts the process mentioned above.

In step 802, the user device (531) reads an electronic document and then displays one or more questions in the electronic document on a display associated with the user device (531).

A user may input answers to the questions, using a keyboard, a virtual keyboard or a mouse, by touching the display or by speaking the answer on a microphone.

In step 803, the user device (531) receives the user's answers to the questions from the user and collects information on answering which was generated by an answer operation by the user (551) during inputting or reviewing the answers.

The user device (531) may generate, from the information on the answers, answer history information for the user's answers. Alternatively, the system (501) may generate answer history information for the user's answers from the information on the answers which were obtained from the user device (531).

In step 804, the system (501) reads, into a memory, the user's answers to the questions and the answer history information for the user's answers.

In step 805, the system (501) inputs, into the first machine learning model (561), the user's answers to the questions and the answer history information for the user's answers to output a first analysis result.

In step 806, the system (501) provides the user's answers to the questions and, optionally, the analysis result to the device (532). The device (532) may present the user's answers to the questions and, optionally, the analysis result to the person (552) associated with the device (532).

The person (552) may judge the user's answers to the questions and then input a result against the user's answers to the questions, if she or he thinks that the first analysis result or the selected one or more items are inappropriate.

In step 807, the system (501) may judge whether the result against the user's answers to the questions was input by the aforesaid person (552). If the judgment is positive, the system (501) may proceed to step 808. Meanwhile, if the judgment is negative, the system (501) may proceed to step 809.

In optional step 808, the system (501), or another system, reads into the memory the result which was obtained by manually judging the answers to the questions.

In step 809, the system (501) inputs, into the second machine learning model (562), the user's answers, the answer history information for the user's answers, the first analysis result, and, if exists, the result which was obtained by manually judging the answers to the questions to output a second analysis result.

In optional step 810, the system (501), or another system, may provide the second analysis result to a device which represents, to a person, the first analysis result or the result which was obtained by manually judging the answers to the questions.

In step 811, the system terminates the process mentioned above.

The system (501) may provide the training data set obtained from the system (501) to a system where the trainings of the first machine learning model (561) and the second machine learning model (562) are performed according to the process described in FIGS. 5B and 5C, respectively.

FIG. 8B illustrates an embodiment of a flowchart corresponding to the diagram described in FIG. 5A. In the embodiment, the first machine learning model (561) and the second machine learning model (562) described in FIG. 5A are prepared according to the flowcharts described in FIGS. 5B and 5C, respectively, prior to a start of the process. The answer history information for the user's answers may be used to obtain a first analysis result from the first machine learning model (561) and further the answer history information for the user's answers may be used to obtain a second analysis result from the second machine learning model (562). Further, the first analysis result may be replaced with the result which was obtained by manually judging the answers to the questions and then the first analysis result, after the replacement, may be provided to a user.

In step 821, the system (501) starts the process mentioned above.

Steps 822 to 827 correspond to steps 802 to 807, respectively. Accordingly, the overlapping explanations of steps 822 to 827 are omitted here.

In step 828, the system (501) reads, into the memory, the result which was obtained by manually judging the answers to the questions. The system (501), or another system, may then replace the first analysis result with the result which was obtained by manually judging the answers to the questions.

In step 829, the system (501) inputs, into the second machine learning model (462), the user's answers, the answer history information for the user's answers, and the first analysis result after the replacement to output a second analysis result.

In optional step 830, the system (501), or another system, may provide the second analysis result to a device which represents, to a person, the first analysis result, or the result which was obtained by manually judging the answers to the questions.

In step 831, the system terminates the process mentioned above.

The system (501) may provide the training data set obtained from the system (501) to a system where the trainings of the first machine learning model (561) and the second machine learning model (562) are performed according to the process described in FIGS. 5B and 5C, respectively.

Figure 9A:
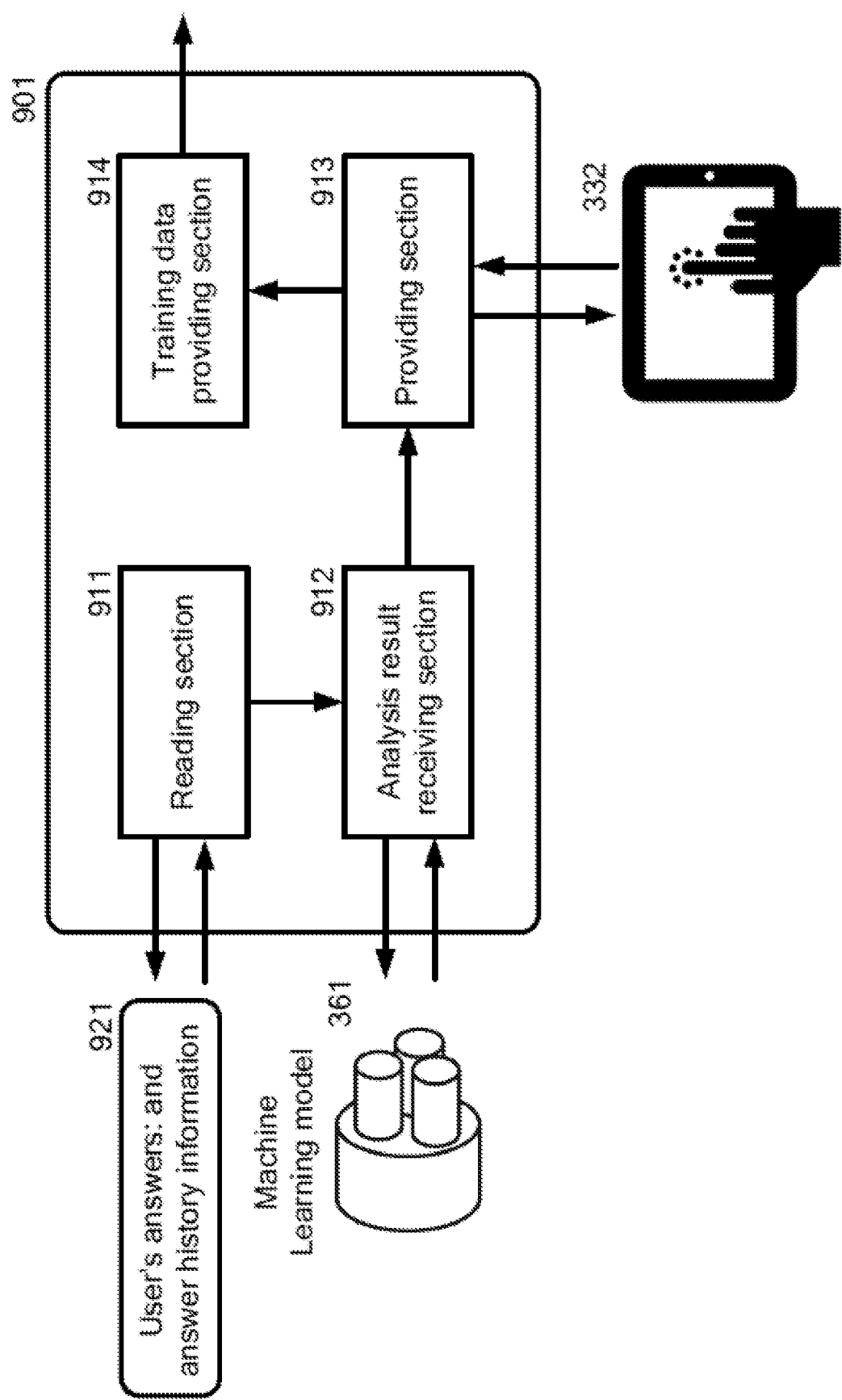
FIG. 9A depicts a functional block diagram of system hardware used in accordance with the embodiment for the flowchart described in FIGS. 6A and 6B.
Figure 9B:
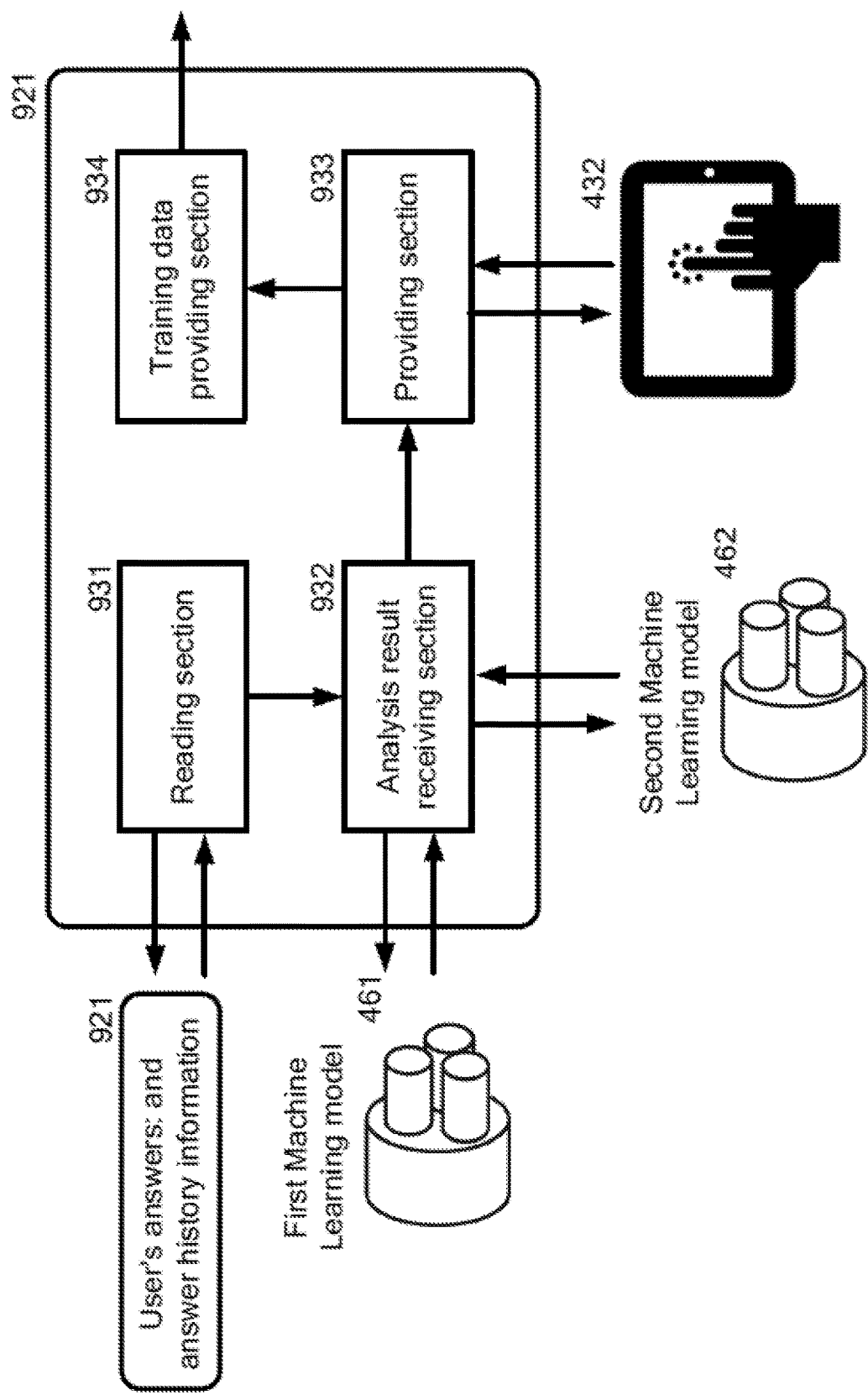
FIG. 9B depicts a functional block diagram of system hardware used in accordance with the embodiment for the flowchart described in FIGS. 7A and 7B.
Figure 9C:
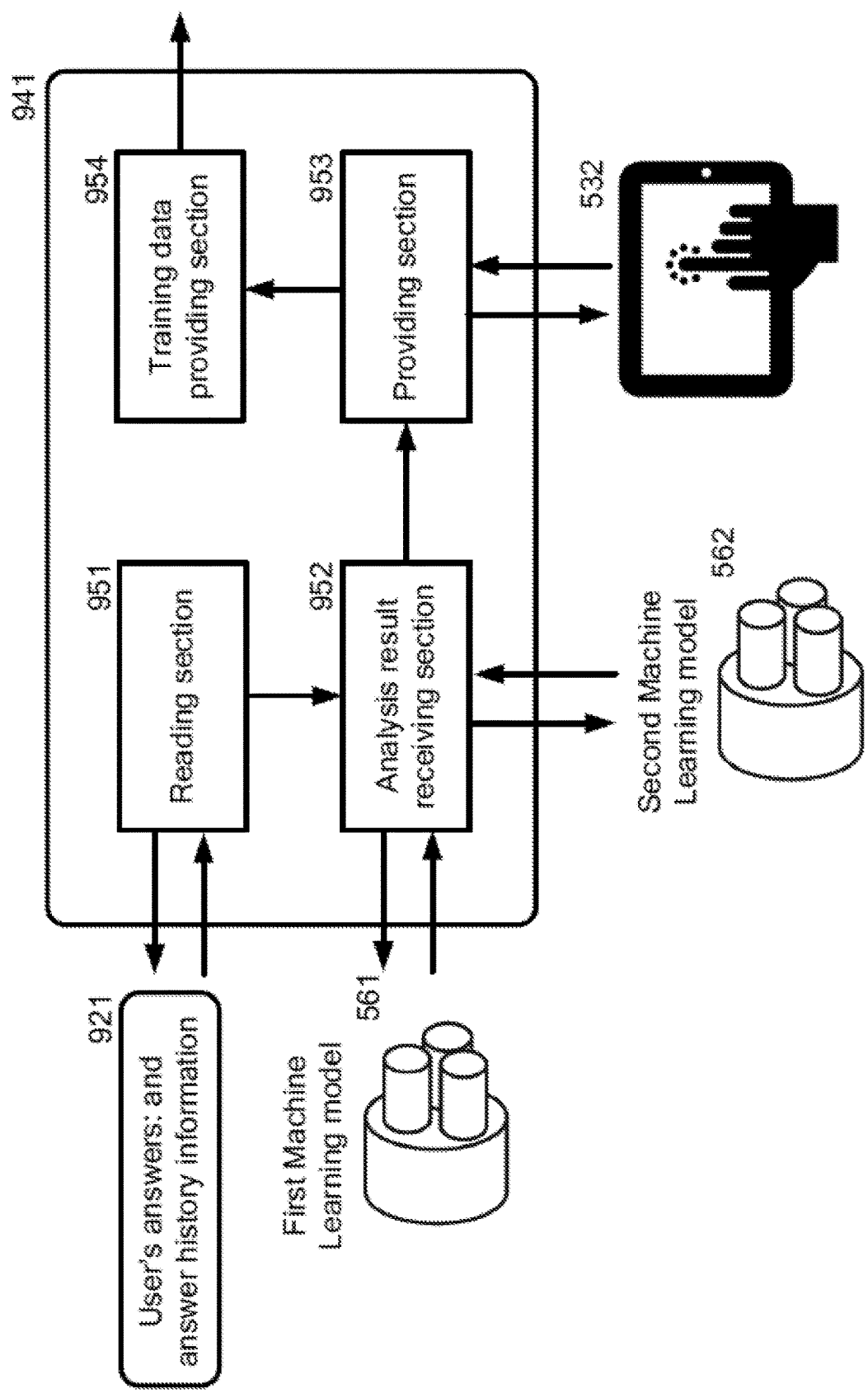
FIG. 9C depicts a functional block diagram of system hardware used in accordance with the embodiment for the flowchart described in FIGS. 8A and 8B.

FIGS. 9A to 9C each depict a functional block diagram of system hardware used in accordance with the embodiment of the overall flowcharts described in FIGS. 6A and 6B, 7A and 7B, and 8A and 8B, respectively.

FIG. 9A depicts an overall functional block diagram according to the flowchart of each of FIGS. 6A and 6B.

The system (901) corresponds to the system (301) described in FIG. 3A.

The system (901) comprises a reading section (911), an analysis result receiving section (912), a providing section (913), and a training data providing section (914).

The reading section (911) reads, into a memory, user's answers to the questions, and answer history information for the user's answers (921).

The reading section (911) may perform step 604 described in FIG. 6A and step 624 described in FIG. 6B.

The analysis result receiving section (912) inputs, into the machine learning model (361), the user's answers to the questions and the answer history information for the user's answers to output an analysis result.

The analysis result receiving section (912) may perform step 605 described in FIG. 6A and step 625 described in FIG. 6B.

The providing section (913) provides the analysis result to the device (332).

The providing section (913) may perform steps 606 and 607 to 609 described in FIG. 6A and steps 626 and 627 to 629 described in FIG. 6B.

The training data providing section (914) may provide the training data set obtained from the system (901) to a system where the training of the machine learning model (361) is performed.

FIG. 9B depicts an overall functional block diagram according to the flowchart of each of FIGS. 7A and 7B.

The system (921) corresponds to the system (401) described in FIG. 4A.

The system (921) comprises a reading section (931), an analysis result receiving section (932), a providing section (933), and a training data providing section (934).

The reading section (931) reads, into a memory, user's answers to the questions, and answer history information for the user's answers (921).

The reading section (931) may perform step 704 described in FIG. 7A and step 724 described in FIG. 7B.

The analysis result receiving section (932) inputs the user's answers to the questions into the first machine learning model (461) to output a first analysis result.

Also, the analysis result receiving section (932) inputs, into the second machine learning model (462), the user's answers to the questions, the answer history information on the user's answer, the first analysis result, and, if exists, the result which was obtained by manually judging the answers to the questions to output a second analysis result.

The analysis result receiving section (932) may perform steps 705 and 707 to 709 described in FIG. 7A and steps 725 and 727 to 729 described in FIG. 7B.

The providing section (933) provides the first analysis result to the device (432). Further, the providing section (933) provides the second analysis result to the device (432).

The providing section (933) may perform steps 706 and 710 described in FIG. 7A and steps 726 and 730 described in FIG. 7B.

The training data providing section (934) may provide the training data set obtained from the system (921) to a system where the trainings of the first machine learning model (461) and the second machine learning model (462) are performed.

FIG. 9C depicts an overall functional block diagram according to the flowchart of each of FIGS. 8A and 8B.

The system (941) corresponds to the system (501) described in FIG. 5A.

The system (941) comprises a reading section (951), an analysis result receiving section (952), a providing section (953), and a training data providing section (954).

The reading section (951) reads, into a memory, user's answers to the questions, and answer history information for the user's answers (921).

The reading section (951) may perform step 804 described in FIG. 8A and step 824 described in FIG. 8B.

The analysis result receiving section (952) inputs, into the first machine learning model (561), the user's answers to the questions and the answer history information for the user's answers to output a first analysis result.

Also, the analysis result receiving section (952) inputs, into the second machine learning model (562), the user's answers, the answer history information for the user's answers, the first analysis result, and, if exists, the result which was obtained by manually judging the answers to the questions to output a second analysis result.

The analysis result receiving section (952) may perform steps 805 and 807 to 809 described in FIG. 8A and steps 825 and 827 to 829 described in FIG. 8B.

The providing section (953) provides the first analysis result to the device (532). Further, the providing section (953) provides the second analysis result to the device (532).

The providing section (953) may perform steps 806 and 810 described in FIG. 8A and steps 826 and 830 described in FIG. 8B.

The training data providing section (954) may provide the training data set obtained from the system (931) to a system where the trainings of the first machine learning model (561) and the second machine learning model (562) are performed.

In an exemplary embodiment, suppose that the medical interview questionnaire, described in FIG. 2A, was prepared in advance. Further, the first machine learning model (461) and the second machine learning model (462) were prepared in advance according to an embodiment described in FIGS. 4B and 4C, respectively. The first machine learning model (461) and the second machine learning model (462) each can output a list of a disease name together with the degree of confidence in response to an input.

The user device (431) reads an electronic document and then displays one or more questions in the electronic document (201) on a display associated with the user device (431).

A patient went to a hospital and was asked to input an answer to each of the questions in the medical interview questionnaire, prior to a doctor's diagnosis.

The patient sees the medical interview questionnaire (201), described in FIG. 2A, through a display associated with the user device (431).

The patient (451) inputs answers to the questions on the user device (431). During inputting the answers by the patient (451), the user device (431) collected information on answering, as described in FIG. 2B, and then sent the user's answers to the questions and the collected information to the system (401).

The system (401) generated answer history information on the user's answers from the information on answering which was sent from the user device (431).

The system (401) input, into the first machine learning model (461), the user's answers to the questions and the answer history information on the user's answers to output a first analysis result. The system (401) obtained the first analysis result, i.e. a list of disease name having the degree of confidence for each listed item. The list of disease may be as follows: Hepatic cirrhosis 0.9, Gout 0.8, Renal failure 0.7, Cerebral infarction 0.6, - - - .

The system (401) selected the top three items among the list of disease name and then sent the selected top three items, i.e. Hepatic cirrhosis 0.9, Gout 0.8, and Renal failure 0.7, to the device (432).

The device (432) received the top three items and then presented the top three items to the doctor (452).

The doctor (452) saw the top three items and, if necessary, the answers to the questions, and then modified the items as follows: "Cerebral infarction" (corresponding to the result which was obtained by manually judging the answers to the questions).

The device (432) sent the result which was obtained by manually judging the answers to the questions, by the doctor, to the system (401).

The system (401) received the result which was obtained by manually judging the answers to the questions from the device (432) and then input, into the second machine learning model (462), the user's answers, the answer history information for the user's answers, the first analysis result, and the result which was obtained by manually judging the answers to the questions (i.e. Cerebral infarction) to output a second analysis result. The system (401) obtained the second analysis result (i.e. a list of disease name having the degree of confidence for each listed item). The list of diseases may now be as follows: Cerebral hemorrhage 0.9, Cerebral infarction 0.8, Hepatic cirrhosis 0.6, Gout 0.4, Renal failure 0.4, - - - .

The system (401) selected the top three items among the list of disease names and then sent the selected top three items, i.e. Cerebral hemorrhage 0.9, Cerebral infarction 0.8, and Hepatic cirrhosis 0.6, to the device (432).

A person skilled in the art may apply this example to a diagnosis and treatment department name, a hospital name, a medicine name, a medical treatment plan, a medical certificate, an inspection name, or a medical personnel name. For example, an electronic document may comprise information on a diagnosis and treatment department name, a hospital name, a medicine name, a medical treatment plan, a medical certificate, an inspection name, or a medical personnel name.

The present invention may be a method, a system, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

By the expression "a/one" should be understood as "at least one".

By the expression "comprise(s)/comprising a/one" should be understood as "comprise(s)/comprising at least one".

By the expression "comprise(s)/comprising" should be understood as "comprise(s)/comprising at least".

By the expression "/" should be understood as "and/or".

What is claimed is:

1. A computer-implemented method for analyzing a user's answers to questions in an electronic document, the method comprising:
    reading, into a memory, the user's answers to the questions and a user's answer history information from the user's answers, wherein the user's answer history information is collected at the time the questions are answered,
        wherein the user's answer history information comprises data from the user's answers to the questions based on an answering order of the questions, and a number of times or frequency that the user's answer to each question is changed, wherein the answer history information on the answering order of the questions includes the answering order faster or slower than a predetermined reference order,
        wherein the user's answer history information comprises biometric information and sensor information of the user's action obtained at the time the questions are answered, wherein the biometric and sensor information are obtained by utilizing at least one biometric sensor and at least one motion sensor, wherein the biometric sensor detects the user's body temperature and the motion sensor detects a speed of the user's answers to the questions; and inputting, into a machine learning model, the user's answers to the questions and the user's answer history information from the user's answers to output an analysis result, wherein the machine learning model is a Convolutional Neural Network configured to predict the analysis result based on the user's answers to the questions and the user's answer history information, wherein the machine learning model is trained, in advance, using one or more sets of training data, each set of training data comprising one or more answers to one or more questions and answer history information from the one or more answers, and a correct result which is obtained by manually judging the one or more answers to the one or more questions wherein the machine learning model is further trained by utilizing the user's answer history information from the user's answers.

2. The computer-implemented method of claim 1, further comprising:

inputting the user's answers into a first machine learning model to output a first analysis result, wherein the first machine learning model is trained, in advance, using one or more sets of training data, each set of training data comprising one or more answers to one or more questions, and answer history information from the one or more answers, and a correct result which is obtained by manually judging the one or more answers to the one or more questions;

inputting, into a second machine learning model, the user's answers, the user's answer history information from the user's answers, and the first analysis result, wherein the second machine learning model is trained, in advance, using one or more sets of training data, each set of training data comprising one or more answers to one or more questions, and answer history information from the one or more answers, an output analysis result which is determined by inputting, into the first machine learning model, the user's answers to the questions and answer history information from the answers, an analysis result which was an output from the second machine learning model in training, and a correct result which is obtained by manually judging the one or more answers to the one or more questions; and outputting a second analysis result.

3. The computer-implemented method of claim 2, wherein the answer history information comprises data from the user's answers to the questions based on an answering order of the questions, a time required for the user to answer each question, a number of times or frequency that the user's answer to each question is changed, or a combination thereof.

4. The computer-implemented method of claim 2, wherein the user's answer history information, comprising biometric information, sensor information, or a combination thereof, is input to the second machine learning model as the user's answer history information from the user's answers, to output the second analysis result.

5. The computer-implemented method of claim 2, wherein the first analysis result is replaced with the correct result which is obtained by manually judging the one or more answers to the one or more questions.

6. The computer-implemented method of claim 2, wherein one or more items having a predetermined threshold in the first analysis result are presented.

7. The computer-implemented method of claim 2, wherein one or more items having a predetermined threshold in the second analysis result are presented.

8. The computer-implemented method of claim 2, wherein the electronic document comprises a medical interview questionnaire or a medical examination questionnaire, and each of the first analysis result and the second analysis result comprise a list of one or more disease names.

9. The computer-implemented method of claim 8, wherein the medical interview questionnaire or the medical examination questionnaire are associated with a diagnosis and treatment department name, a hospital name, a medicine name, a medical treatment plan, a medical certificate, an inspection name, a medical personnel name, or a combination thereof.

10. The computer-implemented method of claim 8, wherein the first analysis result is replaced with a result that is manually judged by a subject matter expert.

11. The computer-implemented method of claim 8, wherein the list comprises a degree of confidence for the one or more disease names.

12. The computer-implemented method of claim 1, further comprising:

inputting, into a first machine learning model, the user's answers to the questions and the user's answer history information to output a first analysis result, wherein the first analysis result is obtained by manually judging the one or more answers to the one or more questions, this manually obtained result being regarded as correct data for analyzing the one or more answers to the one or more questions; and inputting, into a second machine learning model, the user's answers to the questions, the user's answer history information, and the first analysis result itself, or manually judged result of the user's answers to the questions, to output a second analysis result, wherein the second analysis result is an output of the second machine learning model in training, and a result which is obtained by manually judging the one or more answers to the one or more questions, this manually obtained result being regarded as correct data for analyzing the one or more answers to the one or more questions.

13. The computer-implemented method of claim 12, wherein the user's answer history information comprises data from the user's answers to the questions based on an answering order of the questions, a time required for the user to answer each question, a number of times or frequency that the user's answer to each question is changed, or a combination thereof.

14. The computer-implemented method of claim 12, wherein biometric information for the user's action, sensor information for the user's action, or a combination thereof is input into the first machine learning model as the user's answer history information for the user's answers to the questions, in order to output the first analysis result; and biometric information for the user's action, sensor information for the user's action, or a combination thereof is further input into the second machine learning model as the user's answer history information for the user's answers to the questions, in order to output the second analysis result.

15. A computer system, comprising:

a memory storing a program which, when executed on a processor, performs an operation for analyzing answers to questions in an electronic document, the operation comprising:

reading, into a memory, the user's answers to the questions and a user's answer history information from the user's answers, wherein the user's answer history information is collected at the time the questions are answered,
  wherein the user's answer history information comprises data from the user's answers to the questions based on an answering order of the questions, and a number of times or frequency that the user's answer to each question is changed, wherein the answer history information on the answering order of the questions includes the answering order faster or slower than a predetermined reference order,
  wherein the user's answer history information comprises biometric information and sensor information of the user's action obtained at the time the questions are answered, wherein the biometric and sensor information are obtained by utilizing at least one biometric sensor and at least one motion sensor, wherein the biometric sensor detects the user's body temperature and the motion sensor detects a speed of the user's answers to the questions; and
inputting, into a machine learning model, the user's answers to the questions and the user's answer history information from the user's answers to output an analysis result, wherein the machine learning model is a Convolutional Neural Network configured to predict the analysis result based on the user's answers to the questions and the user's answer history information, wherein the machine learning model is trained, in advance, using one or more sets of training data, each set of training data comprising one or more answers to one or more questions and answer history information from the one or more answers, and a correct result which is obtained by manually judging the one or more answers to the one or more questions, wherein the machine learning model is further trained by utilizing the user's answer history information from the user's answers.

16. The computer system of claim 15, further comprising:
inputting, into a first machine learning model, the user's answers to the questions and the user's answer history information to output a first analysis result, wherein the first analysis result is obtained by manually judging the one or more answers to the one or more questions, this manually obtained result being regarded as correct data for analyzing the one or more answers to the one or more questions; and
inputting, into a second machine learning model, the user's answers to the questions, the user's answer history information, and the first analysis result itself, or manually judged result of the user's answers to the questions, to output a second analysis result, wherein the second analysis result is an output of the second machine learning model in training, and a result which is obtained by manually judging the one or more answers to the one or more questions, this manually obtained result being regarded as correct data for analyzing the one or more answers to the one or more questions.

17. A computer program product for analyzing answers to questions in an electronic document, the computer program product comprising a computer readable storage medium having program instructions embodied therewith, wherein the computer readable storage medium is not a transitory signal per se, the program instructions executable by a computer to cause the computer to perform a method comprising:
  reading, into a memory, the user's answers to the questions and a user's answer history information from the user's answers, wherein the user's answer history information is collected at the time the questions are answered,
    wherein the user's answer history information comprises data from the user's answers to the questions based on an answering order of the questions, and a number of times or frequency that the user's answer to each question is changed, wherein the answer history information on the answering order of the questions includes the answering order faster or slower than a predetermined reference order,
    wherein the user's answer history information comprises biometric information and sensor information of the user's action obtained at the time the questions are answered, wherein the biometric and sensor information are obtained by utilizing at least one biometric sensor and at least one motion sensor, wherein the biometric sensor detects the user's body temperature and the motion sensor detects a speed of the user's answers to the questions; and
  inputting, into a machine learning model, the user's answers to the questions and the user's answer history information from the user's answers to output an analysis result, wherein the machine learning model is a Convolutional Neural Network configured to predict the analysis result based on the user's answers to the questions and the user's answer history information, wherein the machine learning model is trained, in advance, using one or more sets of training data, each set of training data comprising one or more answers to one or more questions and answer history information from the one or more answers, and a correct result which is obtained by manually judging the one or more answers to the one or more questions, wherein the machine learning model is further trained by utilizing the user's answer history information from the user's answers.

18. The computer program product of claim 17, further comprising:
  inputting, into a first machine learning model, the user's answers to the questions and the user's answer history information to output a first analysis result, wherein the first analysis result is obtained by manually judging the one or more answers to the one or more questions, this manually obtained result being regarded as correct data for analyzing the one or more answers to the one or more questions; and
  inputting, into a second machine learning model, the user's answers to the questions, the user's answer history information, and the first analysis result itself, or manually judged result of the user's answers to the questions, to output a second analysis result, wherein the second analysis result is an output of the second machine learning model in training, and a result which is obtained by manually judging the one or more answers to the one or more questions, this manually obtained result being regarded as correct data for analyzing the one or more answers to the one or more questions.

* * * * *